(12) United States Patent
Larsen et al.

(10) Patent No.: US 9,937,262 B2
(45) Date of Patent: *Apr. 10, 2018

(54) PRODRUGS OF NAPROXEN AND DICLOFENAC

(71) Applicant: Claus Selch Larsen, Lejre (DK)

(72) Inventors: Claus Selch Larsen, Lejre (DK); Susan Weng Larsen, Rødovre (DK); Mette Agergaard Thing, København (DK); Jesper Langgaard Kristensen, København N (DK); Henrik Jensen, Roskilde (DK); Jesper Østergaard, Farum (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/787,601

(22) PCT Filed: Apr. 28, 2014

(86) PCT No.: PCT/EP2014/058530
§ 371 (c)(1),
(2) Date: Oct. 28, 2015

(87) PCT Pub. No.: WO2014/177479
PCT Pub. Date: Nov. 6, 2014

(65) Prior Publication Data
US 2016/0074523 A1 Mar. 17, 2016

(30) Foreign Application Priority Data

Apr. 30, 2013 (DK) .................................. 2013 70236
May 28, 2013 (DK) .................................. 2013 70289

(51) Int. Cl.
*C07D 233/64* (2006.01)
*C07D 233/54* (2006.01)
(Continued)

(52) U.S. Cl.
CPC ...... *A61K 47/48061* (2013.01); *A61K 31/192* (2013.01); *A61K 31/196* (2013.01); *A61K 45/06* (2013.01); *A61K 47/48023* (2013.01)

(58) Field of Classification Search
CPC .. C07D 233/64; C07D 233/54; C07C 229/58; C07C 229/56; A61K 31/4174; A61K 31/4164; A61K 31/196; A61K 31/192
(Continued)

(56) References Cited

U.S. PATENT DOCUMENTS 8,796,325 B2    8/2014  Boiteau et al.
2014/0315960 A1* 10/2014  Larsen ............. A61K 47/48023
514/357

FOREIGN PATENT DOCUMENTS

WO    WO 2001/62085 A1    8/2001
WO    WO 2012001055 A1 *  1/2012 ........... A61K 9/0014
WO    WO 2013/064153 A1   5/2013

OTHER PUBLICATIONS

Hussain, M. A., A. Zarish, K. Abbas, M. Sher, M. N. Tahir, W. Tremel, M. Amin, A. Ghafoor, and B. A. Lodhi "Hydroxypropylcellulose-aceclofenac conjugates: high covalent loading design, structure characterization, nano-assemblies and thermal kinetics" Cellulose (2013), 20: pp. 717-725.*

(Continued)

*Primary Examiner* — Matthew Coughlin
*Assistant Examiner* — Sagar Patel
(74) *Attorney, Agent, or Firm* — F. Aaron Dubberley

(57) ABSTRACT

The present invention relates to a compound of formula (I): wherein $R_1$ is $R_3$-IPU and $R_2$ is the acyloxy residue of diclofenac or naproxen, and specified by the following structures (A) wherein OH—$R_3$-IPU is selected from (B) and $R_4$ and $R_5$ may be the same or different selected from (C) and salts, solvates and hydrates thereof.

(I)

(A)

(Continued)

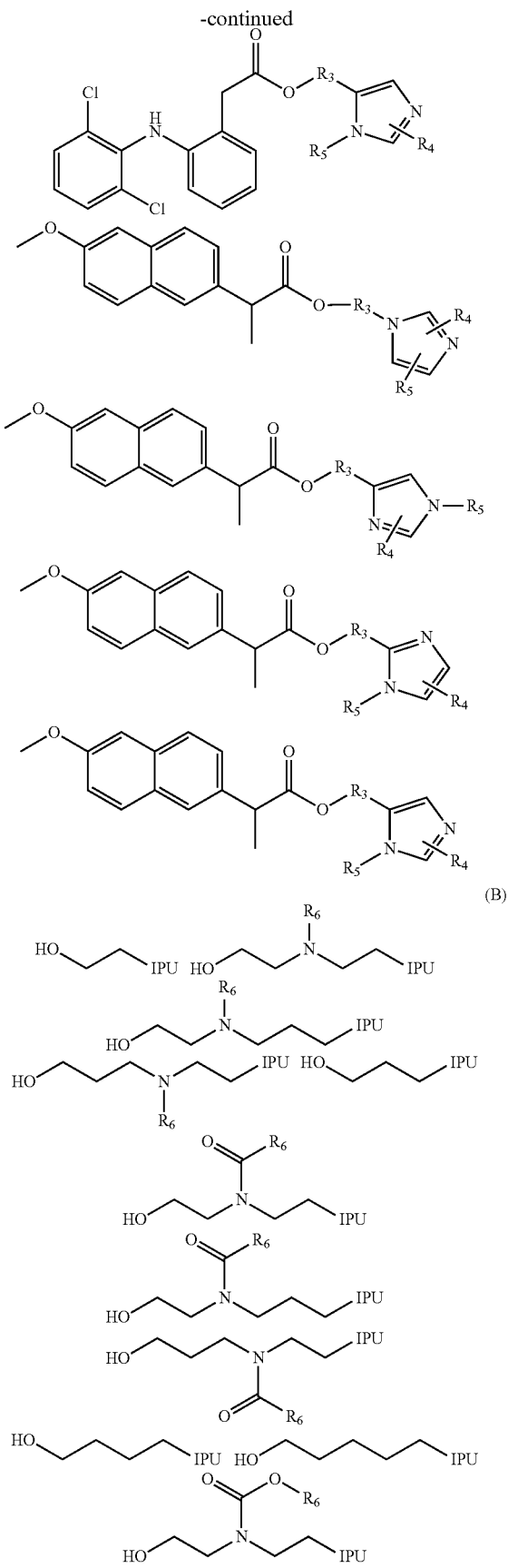
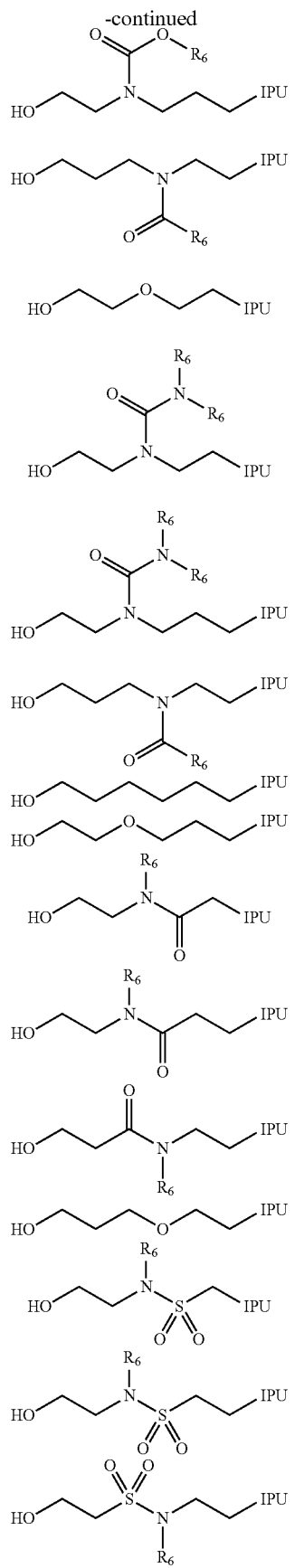

-continued

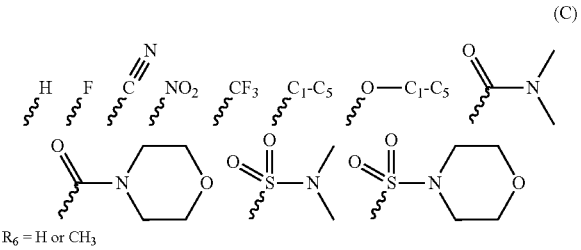

(C)

$R_6$ = H or $CH_3$

17 Claims, 1 Drawing Sheet

(51) Int. Cl.
C07C 229/58 (2006.01)
C07C 229/56 (2006.01)
A61K 31/4174 (2006.01)
A61K 31/4164 (2006.01)
A61K 31/196 (2006.01)
A61K 31/192 (2006.01)
A61K 47/48 (2006.01)
A61K 45/06 (2006.01)

(58) Field of Classification Search
USPC .................. 548/341.1, 335.1; 514/400, 399
See application file for complete search history.

(56) References Cited

OTHER PUBLICATIONS

Rao et al., "Synthesis, insecticidal and antifeedant activities of new type of pyrethroid esters", Indian Journal of Chemistry, vol. 29B, pp. 1034-1040, Nov. 1990.
Rasmussen et al., "Assessment of the Effect of High or Low Protein Diet on the Human Urine Metablome as Measured by NMR," Nutrients, vol. 4, pp. 112-131, Feb. 2012.
Ruiz-Suarez et al., "Postoperative Pain Control After Should Arthroscopy," Orthopedics, vol. 31, Issue 11, pp. 1-10, Nov. 2008.
International Search Report dated Jul. 22, 2014 in application No. PCT/EP2014/058530.
Halen, et al., "Prodrug Designing of NSAIDs", Mini-Reviews in Medicinal Chemistry, 2009, 9:124-139.
Rediguieri, et al., "Biowaiver Monographs for Immediate Release Solid Oral Dosage Forms: Metronidazole", Journal of Pharmaceutical Sciences, 2011, 100(5):1618-27.

* cited by examiner

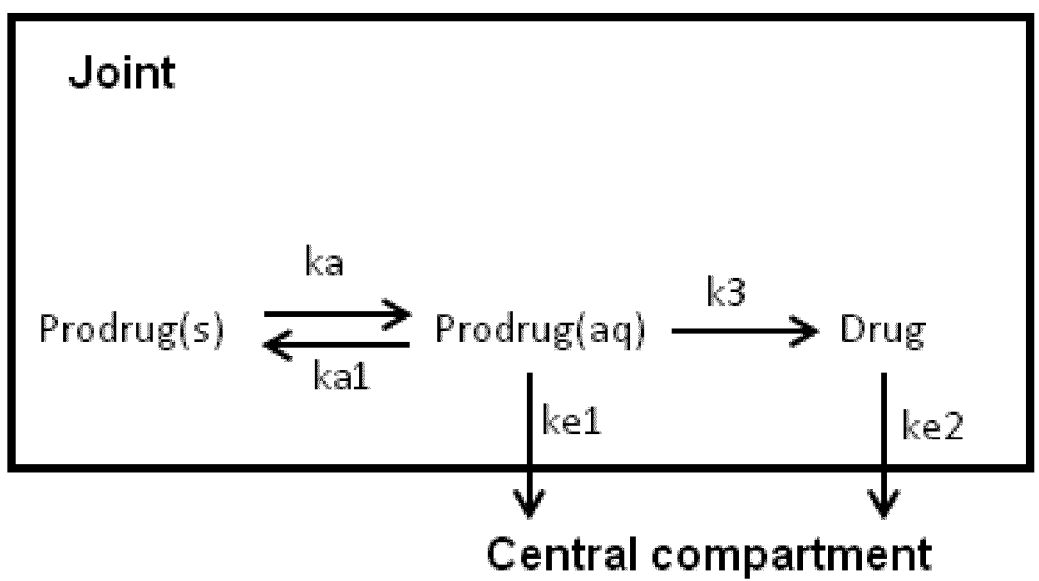

PRODRUGS OF NAPROXEN AND DICLOFENAC

FIELD OF THE INVENTION

The present invention relates to novel prodrugs of specific NSAIDs comprising an immobility promoting unit (IPU) covalently linked to an active pharmaceutical ingredient via a linker, which forms an ester bond. The active pharmaceutical ingredient is an NSAID selected from naproxen and diclofenac. The IPU is a substituted or unsubstituted imidazolyl group. It normally has a $pK_a$ value of between 4 and 7.6 or between 4 and 8.4 including between 7.7 and 8.4 at 37° C. Thus, the novel compounds have a higher solubility at acidic pH compared with neutral or slightly alkaline pH. This difference in solubility at different pH is an important characteristic of the novel compounds as it makes it possible to form a depot of the prodrug in the body after administration as the prodrug is designed to at least partly be present in solid form at the administration site. Thus, the novel compounds are preferably soluble at acidic pH but precipitate at neutral/slightly alkaline pH. Thus, the compounds may be formulated as slightly acidic solutions, but upon injection into a joint the prodrug will precipitate and act as a depot of the drug. In the joint, the prodrug will slowly dissolve and be converted to the active drug substance by hydrolytic enzymes present in the joint. The invention furthermore relates to pharmaceutical compositions of the novel prodrugs, as well as the use of the compounds and compositions as medicaments, and for use in specific treatments of i.a. injured and inflamed joints.

BACKGROUND OF THE INVENTION

Modern postoperative pain control focuses on early mobilization and rapid discharge of patients following surgery. Although minimally invasive of nature, arthroscopic procedures do produce pain and inflammation. As a result patients may be prevented from returning to work for weeks after surgery.

Findings have shown that aggressive pain management, including local intra-articular drug therapy, in the early postoperative period can improve convalescence after surgery significantly.

Over the years the efficacy of a significant number of drugs and drug combinations to provide pain relief after intra-articular injection has been investigated. Efficacious intra-articular monotherapeutic approaches include (i) NSAIDs, (ii) local anaesthetics, and (iii) opiates (e.g. morphine). Following arthroscopic procedures promising pain alleviating effects of different intra-articular multimodal analgesic regimens have been reported. Most combinations used consisted of 2-3 drugs selected from opiates, local anaesthetics and anti-inflammatory agents (NSAIDs or corticosteroids) (ref. 1, 2).

Looking to future intra-articular multimodal therapies, particular attention needs to be paid to tailor the duration of action of the individual therapeutic agents whilst keeping the dose of administered compounds to a minimum.

Treatment of e.g. inflammation with NSAIDs is difficult to attain in a site-specific manner. Consequently, a systemic approach is usually employed, where an oral dose is spread through-out the body, thereby limiting the effective dose at the injured or inflamed site, and increasing the emergence of side effects due to high concentrations of NSAIDs in other areas of the body. Attempts to inject the NSAID locally at the site of treatment will only be effective for a few hours, by which time the water-soluble injected drug will, for practical purposes, have diffused out of the joint space, and into the general circulation. This short half-life of intra-articular disappearance of NSAIDs and other small-molecule drugs, which have a high water solubility at and around physiological pH, is inhibitive for a continuous release/depot effect.

Simple depot suspensions may be thought to be a preferred way to deliver an immobilised drug since a high drug load can be achieved and minimal pharmaceutical excipients are needed. However, in spite of the relative simplicity of this formulation type compared to more advanced and complex controlled release drug delivery systems, the formulation of (physically) stable injectable suspensions with good shelf-life poses considerable manufacturing challenges.

The problem of administering depot formulations to joints has previously been attempted to be solved by injecting for example suspensions made from steroid esters. Various long-acting steroid ester formulations (aqueous microcrystalline suspensions) are marketed for intra-articular injection. The duration of action of such injectables are 2-6 weeks and thus not indicated for postoperative pain control following minor arthroscopic surgery, which is typically 1-7 days. The drawbacks of using a microcrystalline suspension include that suspensions are difficult to sterilize (e.g. sterilization by filtration is excluded) and that the particle size distribution of the suspended particles may change over time, thereby also changing the in vivo drug release profile. Thus, the formulation of (physically) stable injectable suspensions with good shelf-life poses considerable manufacturing challenges.

Alternatives to microcrystalline depot formulations as described above are injecting a poorly water-soluble salt of the drug solubilised in a co-solvent, which is then precipitated in situ at the injected site (upon contact with water/the biologic fluid, in which the salt is poorly soluble). The drawbacks of this approach is that the release profile is difficult to control—either the release is too fast (1-2 hours) or too slow.

Hydrogels have also been employed, as a possible depot formulation principle. One of the drawbacks of hydrogels is that some do leave behind insoluble residual material in the joint, which is undesirable. Further, a hydrogel does not enable simultaneous release of analgesics (local anaesthetics or opiates over a 24 h period) and anti-inflammatory agents (NSAIDs or corticosteroids over about 7 days), which has been found to improve convalescence after surgery significantly.

There is thus a need in the art for intra-articular depot formulations that may be tailored to have a release profile over 1-7 days.

Further, there is a need for a formulation that does not leave behind insoluble residual material in the joint.

Further, there is a need for a formulation that allows the tailoring of different release profiles in a multimodal regimen.

DESCRIPTION OF THE INVENTION

The present invention was made in view of the prior art described above, and the object of the present invention is to provide novel prodrugs of specific NSAIDs which can be formulated to allow the administered drug to be released over e.g. 1-7 days whilst keeping the dose of administered compounds to a minimum.

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

In general, small-molecule solutes (including NSAIDs) are rapidly cleared from the synovial space after intra-articular (IA) injection. The present invention provides prodrug compounds that has a very low solubility at body pH (i.e. 7.4), which means that the compounds will be in solid form at the administration site. The novel compounds may be injected in the form of a solution (i.e. a slightly acidic solution having a pH of from about 2 to about 5; as described herein the pH is normally dependent on the $pK_a$ of the compound and is from about 2 to about 4 pH units below the $pK_a$ of, the novel compound. If the compounds are administered in the form of a solution, the prodrug compounds form precipitates of low solubility when they are injected into the joint cavity, effectively immobilising the prodrug at the site of required action. The precipitates are in equilibrium with a low concentration of dissolved prodrug (see FIG. 1). The parent drug is regenerated from dissolved prodrug following esterase/hydrolase-mediated cleavage of the prodrug ester bond in the injured or inflamed joint cavity, so releasing the active dissolved drug. However, in some situations the solubility of the prodrugs even at slightly acidic pH may not be sufficient to provide a solution, which can provide a therapeutically effective amount of the compound to the administration site. In such situations it may be necessary to inject the novel compounds in the form of e.g. a dispersion including a suspension or an emulsion. However, preferred novel compounds are those which are soluble at slightly acidic pH optionally in combination with a co-solvent. More specifically the novel compounds preferably have a water solubility at pH 3 and 37° C. of at least 1 microgram/ml, preferably at least 10 microgram/ml and even more preferred at least 25 microgram/ml. Due to the slow dissolution process, therapeutic drug concentrations can be maintained in the joint cavity over relevant and extended periods of time mainly dictated by the free fraction concentration of the prodrug in the inflamed synovial fluid. The prodrug derivatives are designed to have a relatively high solubility in slightly acidic solution but this solubility decreases substantially with increasing pH (up to around physiological pH (about pH 7.4)); the prodrugs are obtained by covalent attachment of water-soluble drug compounds via a linker to appropriate IPUs (immobility-promoting units, such as weak bases containing an imidazolyl functional group with a pKa value in the range of about 4 to about 7.6). Thus, injection of prodrug in the form of slightly acidic aqueous solutions into the joint leads to prodrug precipitation in synovial fluid (in situ precipitate formation). Subsequent availability of the active species is dictated by the rate of dissolution of the precipitate and cleavage of dissolved prodrug by action of hydrolases, including esterases present in the synovial fluid of injured and/or inflamed joints.

Depot drugs of the present invention, which are also referred to as prodrugs, may be useful for monotherapies as well as in multimodal analgesia regimens. The duration of action of the administered medicine will be (roughly) inversely proportional to the rate of dissolution of the precipitated prodrug in the synovial fluid; the rate of dissolution is proportional to the solubility of the prodrug, and this latter parameter can be modified by using IPU's having different physicochemical properties—it is therefore possible to match different IPUs to naproxen or diclofenac as drug compounds in order to achieve a variety of desired release profiles.

To solve the problem the present invention provides a compound of formula (I):

wherein $R_1$ is $R_3$-IPU and IPU is a substituted or unsubstituted imidazolyl group having a molecular weight lower than 1500 g/mol such as lower than 1000 g/mol and a $pK_a$ of between 4 and 7.6 at 37° C.; —O—(C=O)—$R_2$ represents an acyloxy residue of the carboxylic acid group of naproxen or diclofenac; and pharmaceutically acceptable salts, solvates and hydrates thereof, and salts formed with the same or different NSAID than the NSAID represented by —O—(C=O)—$R_2$.

The function of the IPU is to immobilise the prodrug of formula (I) so that it precipitates/is in solid form when injected into an area containing a bodily fluid at and around physiological pH, but also such that the prodrug of formula (I) is soluble at slightly acidic pH, such as pH 1.5 to 5 for example between pH 2 and 4, such as pH 3 to 4, for example 3.3, 3.5, 3.7 and 37° C.

By modifying the $R_1$ moiety by selecting one or more nitrogen containing moieties, the prodrug of formula (I) can be tailored to precipitate at physiological pH, and be soluble at a pH that is between 2 to 6 units lower, as explained above.

The prodrug of formula (I) is a small molecule drug, which is a low molecular weight organic compound that is not a polymer. By low molecular weight organic compound is considered a compound that has a molecular weight below 1500 g/mol, such as below 1000 g/mol.

More specifically, the novel compounds have a substituted or unsubstituted imidazolyl group as IPU and is covalently linked to diclofenac or naproxen via a linker such as shown below:

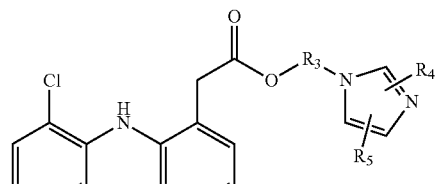

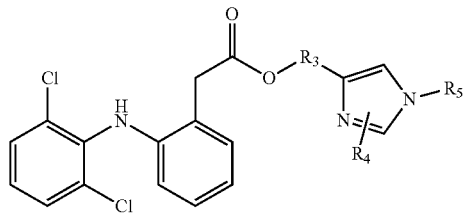

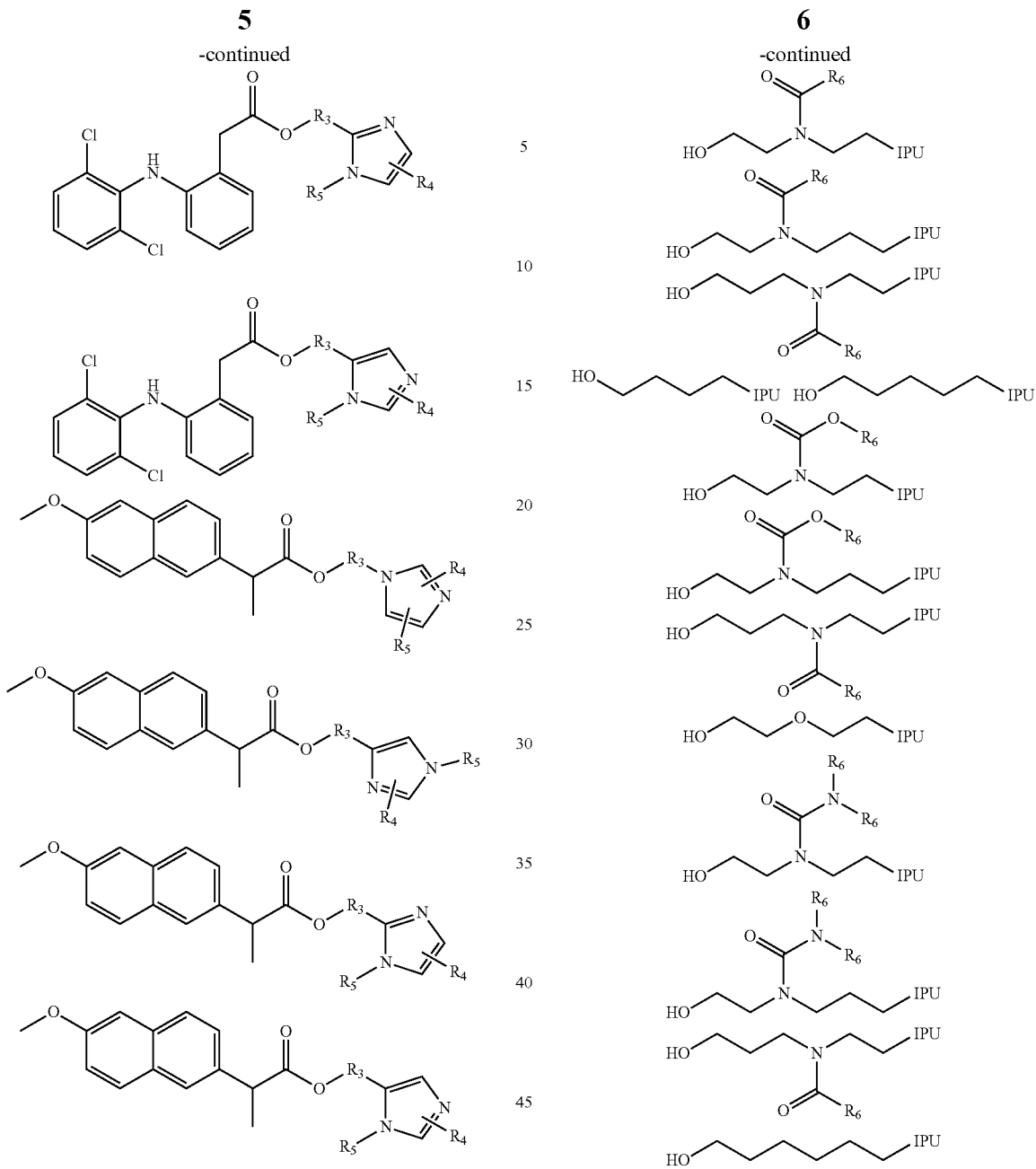
As shown above, the linker may be linked to any relevant position of the imidazolyl group, either to a ring nitrogen or ring carbon atom.
The linker $R_3$ (in the following shown as IPU-$R_3$—OH) may be selected from the following groups:
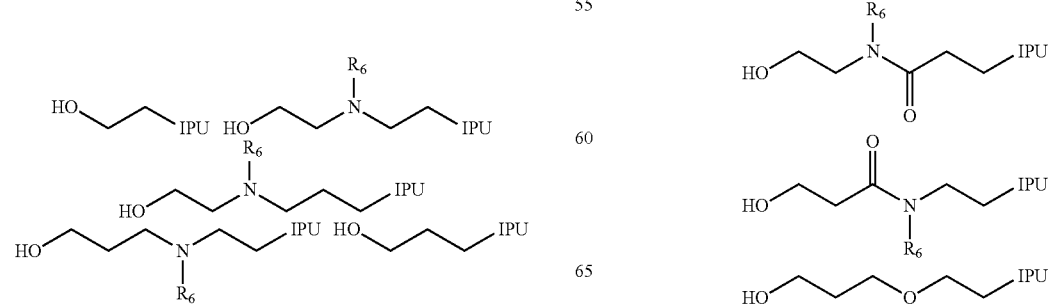

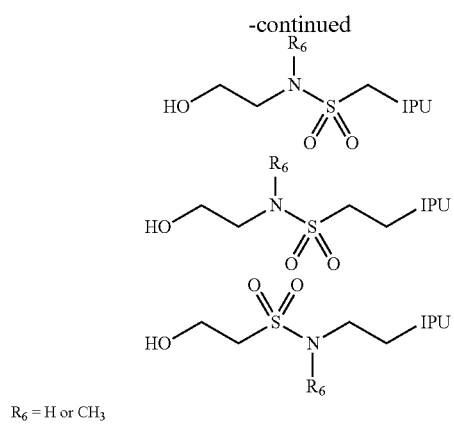

R₆ = H or CH₃

Thus, the linker may be a straight alkyl having from 2 to 6 carbon atoms or it may be an alkyl chain having from 4 to 5 carbon atom containing a heteroatom selected from O or N. It may also contain an amide or sulfoxid function as shown above. The compounds of the invention include any of the R₃ groups shown above (i.e. the IPU indicates the attachment point between R₃ and IPU and the —OH group indicates the attachment point to diclofenac or naproxen.

The imidazolyl group of the IPU has a $pK_a$ value of between 4 and 7.6. It may be selected from substituted or unsubstituted imidazolyl.

The IPU core may contain substituents as indicated by $R_4$ and $R_5$, where $R_4$ and $R_5$ independently of each other are

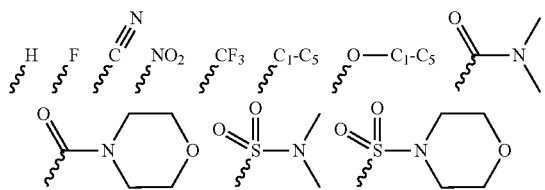

In general it is preferred that $R_4$ and $R_5$ both are H or at least one of $R_4$ and $R_5$ is H, but if the $pK_a$ of the imidazolyl group should be modified in order to e.g. adjust the solubility of the prodrug, the imidazol may be substituted with electron donating groups, which increase the $pK_a$ of the imidazole or electron withdrawing groups that decreases the $pK_a$ of the imidazole.

The substituents $R_4$ and $R_5$ may also contain functional groups or atoms (such as, e.g. oxygen) in order to optimize the hydrophilic-lipophilic balance of the individual prodrug derivative. The positions of the $R_4$ and $R_5$ substituents are interchangeable. In the present context, the term "alkyl" designates $C_{1-5}$ alkyl which may be straight or branched, such as methyl, ethyl, propyl, isopropyl, butyl, isobutyl, tert butyl, pentyl, isopentyl etc.

The imidazolyl group of the novel prodrugs must have a $pK_a$ of between 4 and 7.6 at 37° C. This requirement is important in order to ensure a higher water-solubility at an acidic/slightly acidic pH than at neutral/slightly alkaline pH. To this end, the present inventors have exploited the general knowledge that a certain distance between the N atom and the —O—(C=O)—R₂ can be used to avoid an unwanted effect on the $pK_a$ of the amino group. Thus, the N atom of the imidazolyl group and the —O—(C=O)—R₂ should be separated by a carbon chain containing two or more carbon atoms.

As mentioned above, the IPU (R₁) of the prodrug of formula (I) is an unsubstituted or substituted imidazolyl group. By substitution of the IPU the $pK_a$ can be changed to values of between 4 and 7.6. This may be done by proper manipulation of the moiety by substitution with electron donating groups and/or electron withdrawing groups. Thus, electron donating substituents as alkoxy, phenoxy, amine, alkyl will increase the pKa of the IPU. Consequently, electron withdrawing substituent as aldehydes, ketones, esters, amides, nitrogroups, halogens will lower the pKa. It is well-known to the person skilled in the art to manipulate nitrogen moieties such as for example anilines in this manner to tune the $pK_a$. See for instance the document "*pKa Data Compiled by R. Williams*" (Ref. 3), which can be downloaded from the internet (http://research.chem.psu.edu/brpgroup/pKa_compilation.pdf), and which is the same document that has been cited in the following reference: Caballero et al. (2006) "Theoretical prediction of relative and absolute pKa values of aminopyridines", Biophysical Chemistry 124 (2), p 155-160 (Ref. 4).

Specific compounds of the present invention are:

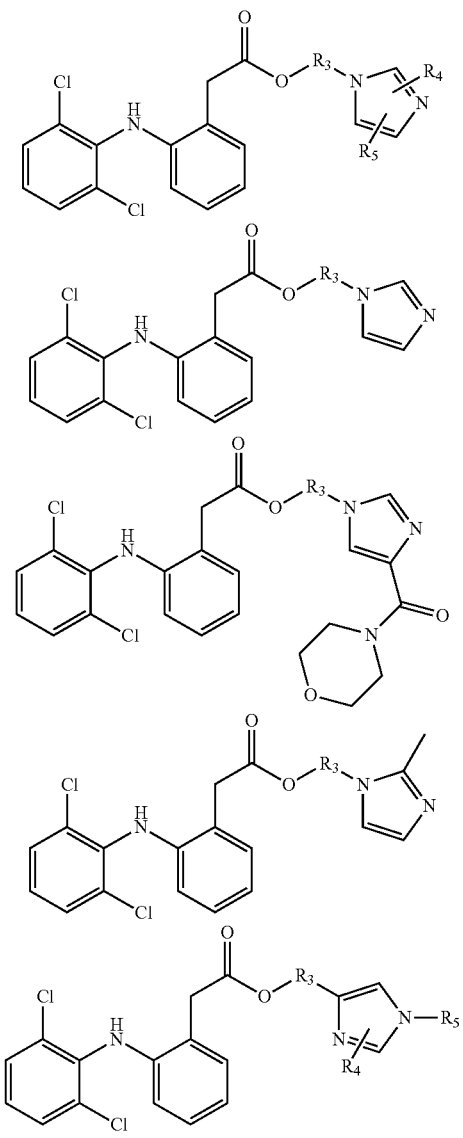

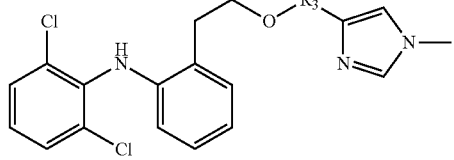
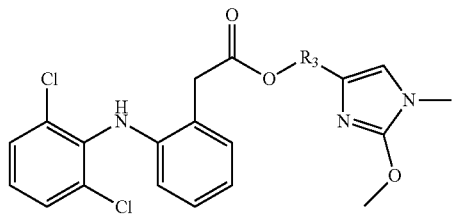
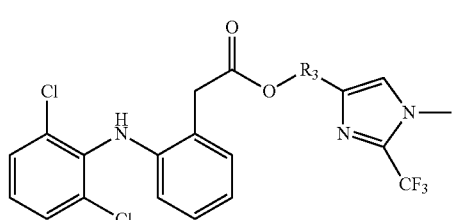
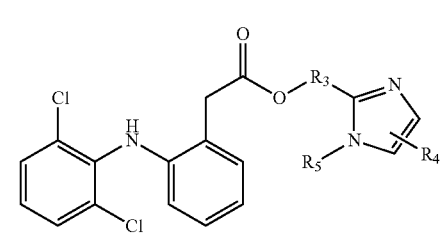
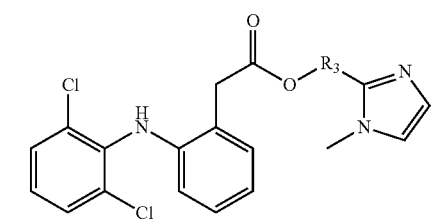
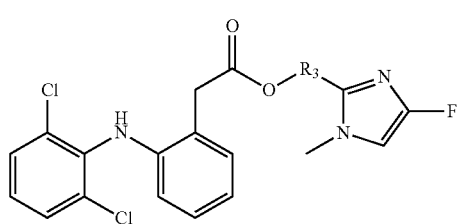
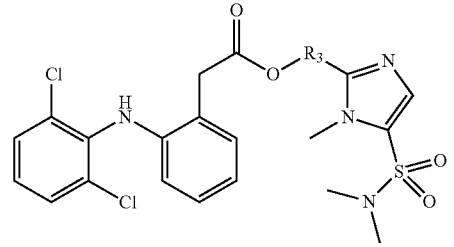

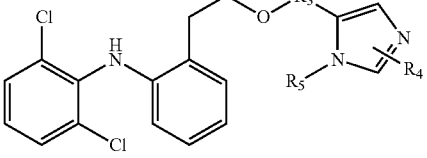
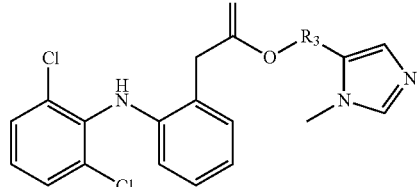
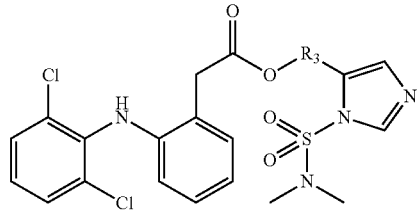
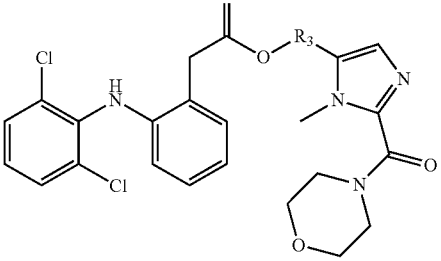

In the formulas above, prodrugs of diclofenac are shown. However, within the scope of the present invention are prodrugs, where naproxen is the active pharmaceutically ingredient.

More specifically and illustrated by compounds DPX-1-0005 to DPX-1-0012 (which are all imidazole derivatives) it is possible to vary:
1) the point of attachment on the Imidazole (see e.g. above)
2) adjust the pKa by varying the substituents on the imidazole (cf above)
3) adjust the solubility of the prodrug by varying the substituents on the imidazole; Increasing the lipophillicity of the IPU will reduce the aqueous solubility of IPU and thus the entire prodrug. If the IPU is substituted with a hydrophilic substituent, the solubility of the IPU and thus the prodrug will increase. Such substituents could be: amines, alcohols, acids, ethers. The nature and length of the linker between the IPU and the NSAID can be used to modify the solubility of the prodrug. Straight chain aliphatic linkers will reduce the solubility of the prodrug the longer they get. Substitution the linker for a hydrophilic linker like polyethylene glycol will increase the solubility of the entire prodrug.
4) The nature and length of the linker between the IPU and the NSAID can also be used to enable spatial separation between the IPU and the drug to allow the hydrolytic enzyme access to the prodrug bond (minimize steric hindrance);
5) how it is possible to combine the permutations independently of each other.

The present invention offers tailored release of active pharmaceutical ingredients—applicable to monotherapy as well as multimodal regimens—and the possibility to tailor their concomitant release.

In general, the prodrugs of the present invention may have a solubility as low as 0.05 µg/ml in 10 mM or 67 mM PBS (phosphate buffer solution) at 37° C. and pH 7.4. In general the solubility is from 0.05 microgram/ml to 1 mg/ml in 10 mM or 67 mM PBS (phosphate buffer solution) at 37° C. and pH 7.4. Based on solubilities determined at pH 7.4, solubilities of prodrugs at pH 3 as high as 100 mg/ml have been estimated. The increase in solubility is theoretically a factor 500, when the pH is decreased with 3 pH units below the $pK_a$ value of the pro-moiety. However, there may be deviations therefrom. Theoretically, prodrugs with an intrinsic solubility (the saturation solubility of the neutral form of the prodrug) of 100 microgram/ml (37° C.) possess solubilities at pH 7.4 (37° C.) of 101, 110, and 200 microgram/ml in case the $pK_a$ value of the prodrug is 5.4, 6.4, and 7.4, respectively. Likewise, in theory a decrease in pH from 7.4 to 3.0 will increase prodrug solubility by a factor of about 250, 2500, and 25000 in case the $pK_a$ of the prodrug is 5.4, 6.4, and 7.4, respectively. Thus, it is important to select prodrugs having suitable balance of $pK_a$ and water solubility at a $pH=pK_a$ in order to obtain the desired dissolution behaviour of the prodrugs a acidic pH and body pH.

The acyloxy residue (—O—(C=O)—$R_2$) is selected from the corresponding carboxylic acid group containing API's belonging to the class of non-steroidal anti-inflammatory agents (NSAIDs) selected from diclofenac and naproxen. Diclofenac is preferred.

The prodrug of formula (I) may be formulated as a pharmaceutically acceptable salt, or as a solvate or hydrate thereof. By pharmaceutically acceptable salts means those salts of compounds of the invention that are safe and effective for injection in mammals, in particular intra-articular injection, and that possess the desired biological activity. Pharmaceutically acceptable salts include salts of basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, oxalate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate salts. Suitable salts are also those formed with the same NSAID as the one included in the prodrug, i.e. if the prodrug is IPU-linker-diclofenac, then a suitable salt is the diclofenac salt of IPU-linker-diclofenac. Suitable salts are also those formed from another NSAID than the one included in the prodrug, i.e. if the prodrug is IPU-linker-diclofenac, then a suitable salt is e.g. the naproxen salt of the IPU-linker-diclofenac prodrug.

The above-mentioned IPUs may all be linked to any of the NSAIDs mentioned herein and the resulting structures are all encompassed by the present invention.

Typical ways of making prodrugs of the formula (I) is by esterification of $R_1$(—OH)$_x$ with the corresponding carboxylic acid (HO—(C=O)—$R_2$) of an active pharmaceutical ingredient (API). However, many other ways of preparing prodrugs of formula (I), i.e. containing an IPU linked to one or more API through ester linkage(s). The ester prodrugs were synthesized using two different methods: Reaction of NSAID acid chlorides with IPU-linker-alcohols or coupling of NSAID carboxylic acids with IPU-alcohols using a dehydrating agent as dicyclocarbodiimide (DCC) or 1-ethyl-3-(3-dimethylaminopropyl)carbodiimide (EDC). Conceivably the prodrugs can also be made from the NSAID carboxylic acid and an alkylation agent under the influence of a suitable base or via acid catalyzed esterification of a NSAID carboxylic acid with and IPU-linker-alcohol.

When the prodrug is soluble, it forms a solution, which is a homogeneous mixture composed of only one phase. When the prodrug precipitates, it forms a heterogeneous mixture composed of a solid phase (e.g. a semi-solid phase) and a liquid phase, where only part of the prodrug is in solution and the rest has precipitated out as a solid (e.g. semi-solid). The solid precipitate may form a crystalline or an amorphous solid.

The prodrugs of the present invention are especially suitable for use in local intra-articular drug therapy.

The solubility of the prodrug of formula (I) at a pH value that is between 2 to 6 units lower than the pH of the physiological fluid it is to be injected into, normally exceeds the corresponding solubility in the physiological fluid it is injected into by at least a factor of 100. Preferably, the solubility is at least 500, such as at least 1000, for example at least 1500 or 2000 times higher than the corresponding solubility in the physiological fluid it is injected into. The physiological fluid may be the synovial fluid, and the volume injected into the synovial fluid may correspond to between 2 and 10% (v/v) or greater of the volume of the synovial fluid. Suitable volumes are normally between 100 µl and up to 2 ml.

A simple way of testing if the solubility is indeed at least 100 times higher than the corresponding solubility in the physiological fluid it is injected into, is to first measure the pH of the physiological fluid that the prodrug of formula (I) is to be injected into. A saturated solution of the prodrug to be measured is made in an aqueous solution at a pH that is between 2 to 6 units lower than the physiological fluid it is to be injected into. Different volumes of this saturated solution is then injected into an aqueous solution at the pH of the physiological fluid that the prodrug is to be injected into, and it is measured if any precipitation occurs, e.g. visually or by other means.

The determination of the solubility of a prodrug at different pH values of interest according to the present invention is carried by adding excess solid prodrug to a container containing a buffer solution with well-defined pH. The mixture is rotated at constant temperature until an equilibrium between solid prodrug and prodrug in solution has established (that is until the prodrug concentration in the supernatant remains constant). At each measurement the pH of the supernatant is controlled and, if needed, adjusted to the desired pH. In a similar manner the solubility of a prodrug in a tissue fluid including the synovial fluid can be determined. The latter procedure comprises a simple way of testing if the solubility at the selected lower pH is indeed at least 100 times higher than the corresponding solubility in the physiological fluid it is injected into. In fact the solubility of DPX-4-0001 amounts to 65 µg/ml at pH 2.02 whereas the solubility of the prodrug decreases 1300-fold to about 0.05 µg/ml at pH 7.4. In contrast the solubility of DPX-2-0007 (derived from another IPU) was determined to approximately 7 mg/ml at pH 3.4 whereas the solubility decreased to 7 µg/ml at pH 7.4. These different pH dependent solubilities may be explained by different pKa values of the prodrugs. For instance, a decrease in pH from pH 7.4 to 2.0 will result in a 1000-fold increase in the solubility of a base with a pKa value of 5, whereas the solubility will increase by a factor of about 9618 for a base with a pKa value of 6.

These predicted alterations in pH dependent solubilities can be calculated from the expression: $S_t=S_0*(1+10^{pKa-pH})$ where $S_t$ is the total solubility at a given pH and $S_0$ is the solubility of the neutral form of the prodrug.

Preferably the bodily fluid at physiological pH is synovial fluid, which is found in the synovial cavity of synovial joints. Physiological pH in this case refers to the intra-articular pH of synovial fluid, which may be from pH 6 to pH 8. In cases not involving acidosis the typical values are from pH 7.0 to 7.6, for example between pH 7.2 to 7.5, such as pH 7.3 to 7.45, for example 7.3, 7.35, 7.4.

In another aspect, the invention provides a pharmaceutical composition, which contains a therapeutically effective amount of a compound according to the present invention, and at least one pharmaceutically acceptable carrier, vehicle and/or adjuvant.

The prodrug of formula (I) may be dissolved or dispersed in an aqueous vehicle and the solution or dispersion is made slightly acidic by addition of a calculated amount of an appropriate acid, such as hydrochloric acid to provide a pharmaceutical composition. Such pharmaceutical composition would also be suitable for intra-articular injection. Optionally, a suitable cosolvent might be added to optimize prodrug solubility. Examples of suitable cosolvents are N,N-dimethylacetamide, N-methylpyrrolidone, dimethyl-sulphoxide (DMSO), polyethylene glycol (PEG 200, PEG 400), propylene glycol, isopropanol, propanol, ethanol and mixtures thereof.

Further, the composition may comprise a dry powder of the prodrug of formula (I) or salt of prodrug to be reconstituted in an appropriate aqueous vehicle just prior to injection.

In some embodiments of the invention, the compounds or pharmaceutical compositions are for use as a medicament, and in other embodiments of the invention, for use in treatment of inflammation in joints, for use in treatment of osteoarthritis and analogous affections. In yet further embodiments the compounds or pharmaceutical compositions are for use in the treatment of postoperative pain following arthroscopic surgery.

The novel compounds and the pharmaceutical compositions of the present invention may be used in medicine such as, e.g. in the treatment of postoperative pain/inflammation following arthroscopic procedures as well as in the management of inflammation in joints or in osteoarthritis associated pain and may accordingly be designed in a form that is suitable for intra-articular injection.

Treating the pathological condition postoperative pain following arthroscopic surgery, involves the treatment of both inflammation and pain, which means that at least one type of API covalently attached via a linker to an IPU with an ester bond is relevant, preferably selected from NSAIDs.

In another aspect, the invention provides a method for the preparation of a novel prodrug according to the invention and a method for the preparation of a medicament with anti-inflammatory and pain relieving activity, characterized in that it comprises a prodrug according to the present invention and one or more pharmaceutically acceptable excipients.

Treating the pathological condition inflammation in joints, such as osteoarthritis and analogous affections, involves the treatment of both inflammation and pain which means that at least one type of API covalently attached to an IPU with an ester bond is relevant, preferably selected from NSAIDs The prodrugs of formula (I) may be used in mammals, preferably humans, horses and dogs.

When describing the embodiments and aspects of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

All particulars and details described herein for the main aspect apply in its entirety to all other aspects.

Other Aspect of the Invention

The prodrugs of the invention may be used in combination with other drug substances to optimize local pain relieving effect e.g. after minor joint surgery.

Modern postoperative pain control focuses on early mobilization and rapid discharge of patients following surgery. Joints are discrete anatomical compartments feasible for local injection of pain alleviating drugs. Although minimally invasive of nature, arthroscopic procedures do produce pain and inflammation. As a result may be prevented from returning to work for up to 2 weeks after surgery. Findings suggest that aggressive pain management (including local IA drug therapies) in the early postoperative period can improve convalescence after arthroscopy. Over the years various IA monotherapeutic approaches have been reasonably effective including nonsteroidal anti-inflammatory drugs (NSAIDs such as diclofenac and naproxen), local anaesthetics (such as bupivacaine and ropivacaine), and strong analgesics (such as morphine and oxycontin). A reasonable degree of consensus has, however, been reached that total postoperative pain relief is not achievable by use of a single agent or method. Therefore guidelines recommend pain management based on the use of multimodal analgesia approaches wherever possible. Multimodal analgesia involves the use of two or more analgesic drugs differing with respect to mechanism of action. Following arthroscopic procedures promising pain alleviating effects of different IA multimodal analgesic regiments have been reported. Most of the combinations have involved the use of 2-3 drugs selected from the above mentioned groups comprising local anaesthetics, NSAIDs, and opioids. However, in the approached investigated no attention has been paid to the optimization of the duration of action of the individual therapeutic agents. It has been suggested that optimal pain relief after minor joint surgery requires analgesic and anti-inflammatory action locally at the site of trauma over about 1 and 7 days, respectively (for a comprehensive treatise of the subject please see the review by Larsen et al. (2008) J Pharm Sci 97, 4622-4654).

Optimal local pain relieving effect after minor joint surgery by use of the NSAID prodrugs of the present in combination local anaesthetics such as bupivacaine or ropivacaine in a multimodal analgesic manner where duration of action of the individual therapeutic agents have been optimized. At completion of surgery marketed injection solutions of the local anaesthetic agent (e.g. Marcain® or Marcain-Adrenalin®) might be injected IA followed by inject of the NSAID prodrug depot injectable. The two injectables might feasibly be purchased as a kit. Alternatively, a slightly acidic injection solution comprising both the local anaesthetic agent and the NSAID prodrug might be administered IA to provide the desired multimodal analgesia. Thus, the prodrugs of the present invention may be used in combined therapy with one of one local anaesthetic agents selected from: amethocaine, chlorprocaine, etidocaine, lidocaine, bupivacaine, mepivacaine, prilocaine, ropivacaine, and procaine.

and/or the prodrugs of the present invention may be used in combined therapy with one or more opiod or strong analgesic selected from: alfentanil, alphaprodine, anileridine, buprenorphine, buturphenol, codeine, dextromoramide, dextropropoxyphene, dihydrocodeine, fentanyl, dydrocodone, hydromorphone, ketobemidone, meptazinol, methadone, morphine, oxycodone, oxymorphone, pentazocine, pethidine, phenazocine, phenoperidine, and sulfentanil.

The drug/prodrugs may be administered in a single composition or in separate compositions e.g. provided as a kit containing two or three containers each containing a composition of i) the prodrug and at least one of ii) a local anaesthetic agent and iii) an opiod. The individual compositions may be combined before administration.

The dosing of the local anaesthetic and/or the opioid for local pain management in connection with arthroscopic joint surgery is well-known to the person skilled in the art.

BRIEF DESCRIPTION OF THE DRAWING

FIG. 1 shows factors influencing the pharmacokinetic fate of the prodrug/drug after administration of the prodrug into the joint. The prodrug dissolved is converted into the active drug by enzymatic cleavage of the prodrug bond.

The invention is illustrated in, but not limited to, the following examples

EXAMPLES

The inventors have tested a number of compounds/prodrugs. The prodrugs were tested according to the "method for testing solubility" below. As expected, all prodrugs exhibited a low although variable solubility at pH 7.4 (due to the very low solubility of the neutral form of the prodrugs).

Standard procedures were used to synthesize the ester derivatives as apparent from the more detailed description of the synthesis of the NSAID ester prodrugs presented below. Purity of the synthesized derivatives exceeded 95% as assessed by $^1$H-NMR and HPLC.

Method for Testing Solubility

The determination of the solubility of a prodrug at different pH values of interest according to the present invention is carried by adding excess solid prodrug to a container containing a buffer solution with well-defined pH. The mixture is rotated at constant temperature until an equilibrium between solid prodrug and prodrug in solution has established (that is until the prodrug concentration in the supernatant remains constant). At each measurement the pH of the supernatant is controlled and eventually adjusted to the desired pH. In a similar manner the solubility of a prodrug in a tissue fluid including the synovial fluid can be determined.

The following examples illustrate general methods for the preparation of prodrugs and the compounds according to the present invention can be prepared in analogous matter using the desired OH—R$_3$ and IPU moieties.

The following compounds are illustrated:

Examples of prodrugs of the invention, where the NSAID is diclofenac:

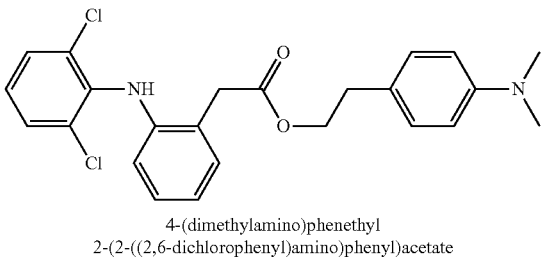

DPX-1-0001

4-(dimethylamino)phenethyl
2-(2-((2,6-dichlorophenyl)amino)phenyl)acetate

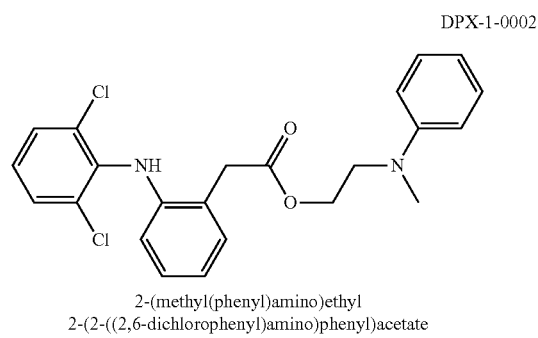

DPX-1-0002

2-(methyl(phenyl)amino)ethyl
2-(2-((2,6-dichlorophenyl)amino)phenyl)acetate

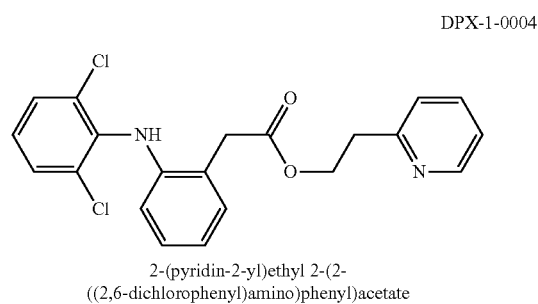

DPX-1-0004

2-(pyridin-2-yl)ethyl 2-(2-
((2,6-dichlorophenyl)amino)phenyl)acetate

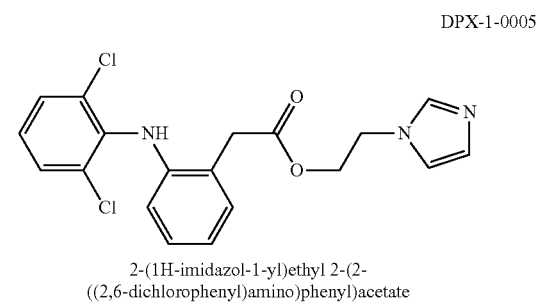

DPX-1-0005

2-(1H-imidazol-1-yl)ethyl 2-(2-
((2,6-dichlorophenyl)amino)phenyl)acetate

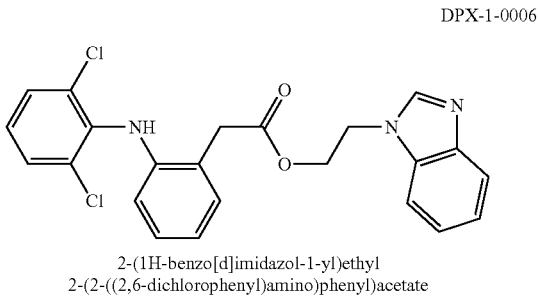

DPX-1-0006

2-(1H-benzo[d]imidazol-1-yl)ethyl
2-(2-((2,6-dichlorophenyl)amino)phenyl)acetate -continued

DPX-1-0007

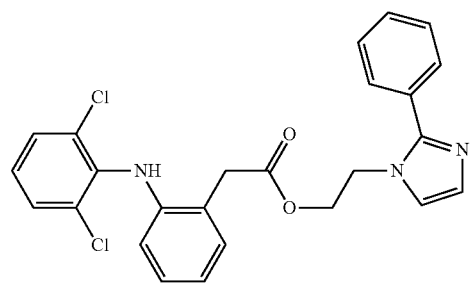

2-(2-phenyl-1H-imidazol-1-yl)ethyl
2-(2-((2,6-dichlorophenyl)amino)phenyl)acetate

DPX-1-0008

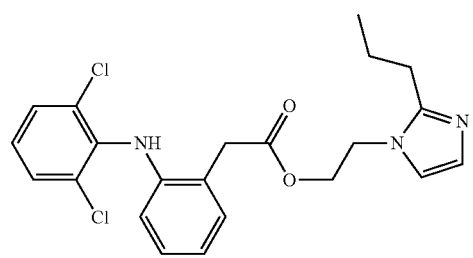

2-(2-propyl-1H-imidazol-1-yl)ethyl
2-(2-((2,6-dichlorophenyl)amino)phenyl)acetate

DPX-1-0009

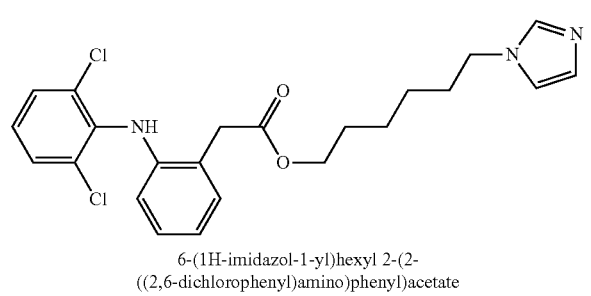

6-(1H-imidazol-1-yl)hexyl 2-(2-
((2,6-dichlorophenyl)amino)phenyl)acetate

DPX-1-0010

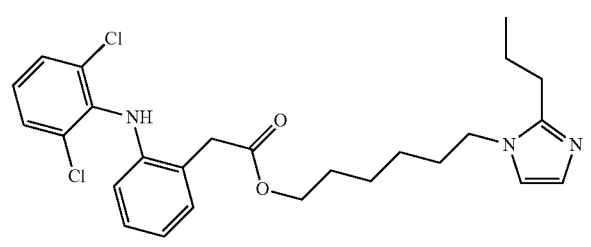

6-(2-propyl-1H-imidazol-1-yl)hexyl 2-(2-
((2,6-dichlorophenyl)amino)phenyl)acetate

DPX-1-0011

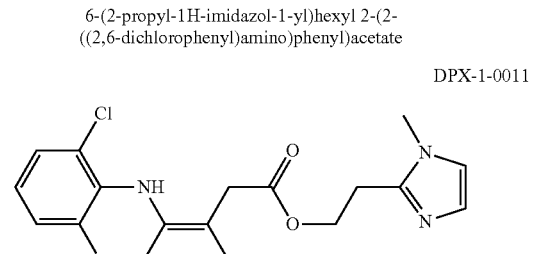

2-(1-methyl-1H-imidazol-2-yl)ethyl 2-
(2-((2,6-dichlorophenyl)amino)phenyl)acetate -continued

DPX-1-0012

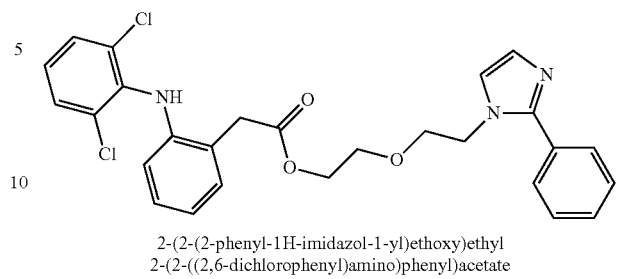

2-(2-(2-phenyl-1H-imidazol-1-yl)ethoxy)ethyl
2-(2-((2,6-dichlorophenyl)amino)phenyl)acetate Examples of prodrugs of the invention where the NSAID is naproxen:

DPX-2-0001

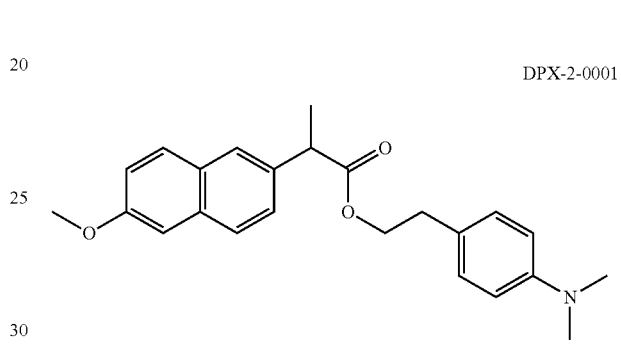

4-(dimethylamino)phenethyl
2-(6-methoxynaphthalen-2-yl)propanoate

DPX-2-0002

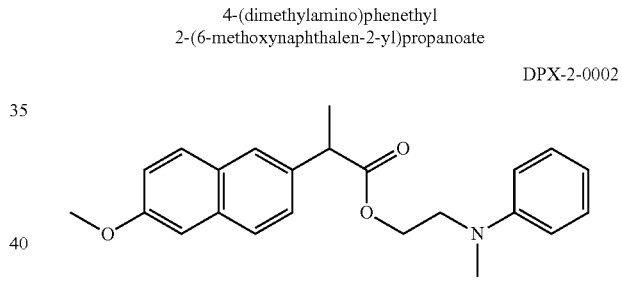

2-(methyl(phenyl)amino)ethyl
2-(6-methoxynaphthalen-2-yl)propanoate

DPX-2-0004

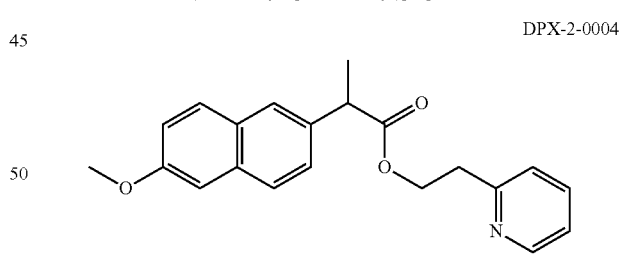

2-(pyridin-2-yl)ethyl 2-(6-methoxynaphthalen-2-yl)propanoate

DPX-2-0003

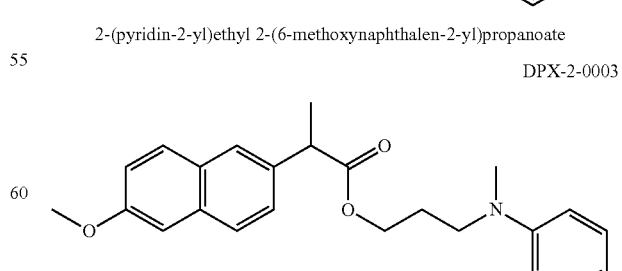

3-(methyl(phenyl)amino)propyl
2-(6-methoxynaphthalen-2-yl)propanoate

-continued

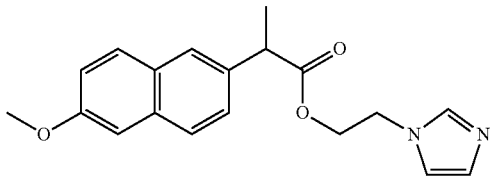

DPX-2-0005

2-(1H-imidazol-1-yl)ethyl
2-(6-methoxynaphthalen-2-yl)propanoate

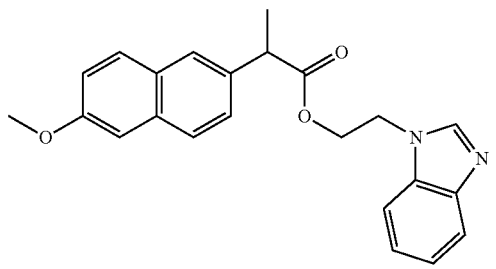

DPX-2-0006

2-(1H-benzo[d]imidazol-1-yl)ethyl
2-(6-methoxynaphthalen-2-yl)propanoate

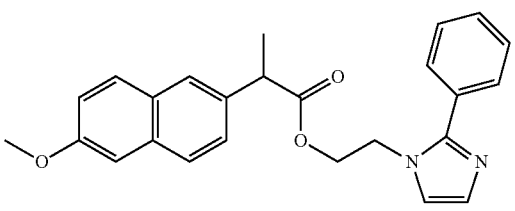

DPX-2-0007

2-(2-phenyl-1H-imidazol-1-yl)ethyl
2-(6-methoxynaphthalen-2-yl)propanoate

These compounds are as far as they are covered by a co-pending, unpublished PCT application not part of the present application.

Example 1: DPX-1-0001 (ALE463)

4-(dimethylamino)phenethyl 2-(2-(2,6-dichlorophenylamino)phenyl)acetate 2-(4-(dimethylamino)phenyl)ethanol (3.3 mmol, 0.55 g), and Dichlofenac (3.3 mmol, 0.99 g) was suspended in dichloromethane (30 mL) under $N_2$ and Dicyclohexylcarbodiimid (6.6 mmol, 1.36 g), 4-Dimethylaminopyridine (0.33 mmol, 36 mg) was added. The mixture was stirred overnight before being poured into sat. $NH_4Cl$ (100 mL) and extracted with dichloromethane (4×50 mL). Drying, filtration and evaporation gave 2.4 g crude material which was purified by Flash Chromatography using EtOAc and Heptanes as eluent giving 0.65 g (43%) of the desired compound. 1H NMR (400 MHz, DMSO-d6) 7.52 (d, J=8.03 Hz, 4H), 7.13-7.24 (m, 4H), 7.04-7.10 (m, 2H), 6.93-7.02 (m, 5H), 6.85 (dt, J=1.25, 7.40 Hz, 2H), 6.58-6.63 (m, 4H), 6.26 (d, J=7.53 Hz, 1H), 4.21 (t, J=7.03 Hz, 4H), 3.78 (s, 2H), 2.82 (s, 11H), 2.77 (t, J=7.03 Hz, 4H) 13C NMR (400 MHz, DMSO-d6) 171.40, 137.07, 130.90, 129.28, 125.86, 123.20, 112.53, 65.51, 37.11, 33.40.

Example 2: DPX-1-0002 (ALE 482)

2-(methyl(phenyl)amino)ethyl 2-(2-(2,6-dichlorophenylamino)phenyl)acetate

Using an Identical Procedure as Described for DPX-1-0001:

2-(methyl(phenyl)amino)ethanol (3.3 mmol, 0.50 g), Dichlofenac (3.3 mmol, 0.99 g), Dichclohexylcarbodiimid (6.6 mmol, 1.36 g), 4-Dimethylaminopyridine (0.3 mmol, 36 mg) and dichloromethane (30 mL). Crude yield: 1.4 g; yield after Flash Chromatography using ethyl acetate and heptanes as eluent: 0.83 g (59%). $^1$H NMR (400 MHz, DMSO-d6) δ 7.52 (d, J=8.28 Hz, 3H), 7.20 (t, J=8.16 Hz, 2H), 7.10-7.15 (m, 4H), 7.05 (dt, J=1.51, 7.78 Hz, 2H), 6.97 (s, 1H), 6.83 (dt, J=1.25, 7.40 Hz, 2H), 6.66-6.72 (m, 3H), 6.56-6.63 (m, 2H), 6.25 (d, J=8.03 Hz, 1H), 4.24 (t, J=5.77 Hz, 3H), 3.74 (s, 3H), 3.58 (t, J=5.77 Hz, 3H), 2.83 (s, 5H). $^{13}$C NMR (400 MHz, DMSO-d6) δ 171.43, 148.71, 142.81, 137.06, 129.13, 128.94, 127.71, 123.02, 115.89, 111.98, 61.90, 50.24, 38.15, 37.02, 31.23, 28.34, 22.07, Methanesulfonate Salt of DPX-1-0002.

Methanesulfonic acid (113 μl, 167 mg, mmol) in dry diethyl ether (10 mL) was added by syringe to a magnetically stirred solution of 2-(methyl(phenyl)amino)ethyl 2-(2-(2,6-dichlorophenylamino)phenyl)acetate (746 mg, 1.74 mmol) in dry diethyl ether (20 mL) under nitrogen cooled in an ice bath. The resulting precipitate in the form of a sticky gum was isolated by decanting off the solvent and washing the gum with dry ether (10 mL). The gum was dried under high vacuum and crystallized from ethanol to afford the title compound as a colourless solid (653 mg). Mp. 143.6-144.6° C. (dec.) (ethanol). $^1$H NMR (400 MHz, DMSO) δ 7.53 (d, J=8 Hz, 2H), 7.27-6.78 (m, 11H), 6.26 (dd, J=8.0, 1 Hz, 1H), 4.23 (t, J=5.5 Hz, 2H), 3.75 (s, 2H), 3.68 (t, J=5.5 Hz, 2H), 2.95 (s, 3H), 2.45 (s, 3H). $^{13}$C NMR (101 MHz, DMSO) δ 171.31, 142.83, 137.04, 131.01, 130.73, 129.26, 129.15, 127.76, 125.95, 122.93, 120.59, 115.83, 114.22, 61.21, 51.76, 39.70 (CH3), 36.94. DEPT $^{13}$C NMR (101 MHz, DMSO) δ 131.01, 129.27, 129.16, 127.77, 125.96, 120.60, 115.84, 61.22, 39.70, 36.94.

Example 3: DPX-1-0004 (sdnX-20)

2-(pyridin-2-yl)ethyl 2-(2-((2,6-dichlorophenyl)amino)phenyl)acetate

Using an Identical Procedure as Described for DPX-1-0001:

2-(pyridin-2-yl)ethanol (37.7 mmol, 4.65 g), Dichlofenac (9.43 mmol, 3.0 g), 4-Dimethylaminopyridin (0.3 mmol, 35 mg), 1-Ethyl-3-(3-dimethylaminopropyl) carbodiimide-HCl (11.32 mmol, 2.17 g), Dichloromethane (15 mL) and Dimethylformamide (10 mL). Yield after Flash Chromatography using ethyl acetate and heptanes as eluent: 1.67 g. The solid HCl-salt was prepared by passing a stream of HCl through an ethereal solution of the product. $^1$H NMR (CDCl$_3$) 3.3-3.7 (m, 4H), 4.58 (br s, 2H), 6.24-7.30 (m, 8H), 7.60 (br s, 1H), 7.97 (br s, 1H), 8.57 (br s, 1H). $^{13}$C (CDCl$_3$): 13.76, 22.29, 25.24, 28.61, 30.62, 31.47, 32.39, 38.03, 62.30, 67.58, 111.37, 121.53, 123.17, 124.30, 124.77, 127.39, 127.81, 128.51, 128.59, 129.42, 130.78, 136.85, 140.77, 142.26, 145.15, 153.05.

Example 4: DPX-1-0005 (ALE460-2)

2-(1H-imidazol-1-yl)ethyl 2-(2-(2,6-dichlorophenylamino)phenyl)acetate

Using an Identical Procedure as Described for DPX-1-0001:

2-(1H-imidazol-1-yl)ethanol (12 mmol, 1.3 g), Dichlofenac (6 mmol, 1.77 g), Dimethylaminopyridin (0.3 mmol, 22 mg), Dicyclohexylcarbodiimid (7.2 mmol, 1.5 g) and Dichloromethane (50 mL). Crude yield: 2.13 g; yield after Flash Chromatography using ethyl acetate and heptanes as eluent: 0.80 g (34%). $^1$H NMR (400 MHz, DMSO-d6) δ 7.58 (t, J=1.00 Hz, 3H), 7.50-7.55 (m, 6H), 7.13-7.27 (m, 7H), 7.09 (t, J=1.25 Hz, 3H), 7.06 (dt, J=1.51, 7.65 Hz, 3H), 7.02 (s, 3H), 6.81-6.87 (m, 6H), 6.24 (d, J=7.53 Hz, 1H), 4.30-4.35 (m, 6H), 4.21-4.26 (m, 6H), 3.82 (s, 2H)$^{13}$C NMR (400 MHz, DMSO-d6) 171.14, 142.85, 137.46, 130.92, 129.13, 127.75, 122.80, 120.50, 119.58, 115.70, 63.98, 45.02, 36.74, 33.33.

Example 5: DPX-1-0006 (JBX022)

2-(1H-benzo[d]imidazol-1-yl)ethyl 2-(2-((2,6-dichlorophenyl)amino)phenyl)acetate 1-Ethyl-3-(3-dimethylaminopropyl)carbodiimide-HCl (1.10 g, 5.74 mmol) was added solid all at once to a magnetically stirred solution of diclofenac (1.48 g, 5.00 mmol), 2-(1H-benzo[d]imidazol-1-yl)ethanol (0.810 g, 10.0 mmol) and 4-Dimethylaminopyridine (31 mg, 0.25 mmol) in dry Tetrahydrofuran (30 mL) cooled in an ice bath and kept under nitrogen. The reaction mixture was stirred in an ice bath for 1 hour and then at ambient temperature. After stirring for 24 hours at room temperature the mixture was concentrated and the residue partitioned between water (25 mL), saturated NH$_4$Cl (25 mL) and EtOAc (100 mL). The organic layer was washed with 50% saturated NH$_4$Cl (2×40 mL), 50% saturated NaHCO$_3$ (40 mL) and brine (50 mL). The organic layer was dried and concentrated. Flash Chromatography using ethyl acetate and heptanes as eluent afforded a colourless oil that crystallised from ether (1.53 g) and was recrystallised to afford the title compound as a colourless solid (1.25 g, 57%). Mp. 128.8-129.3° C. (EtOAc-heptane). $^1$H NMR (400 MHz, DMSO) δ 8.15 (s, 1H), 7.65-7.60 (m, 2H), 7.51 (d, J=8.0 Hz, 2H), 7.29-7.15 (m, 3H), 7.09-7.01 (m, 2H), 6.94 (s, 1H), 6.80 (td, J=7.5, 1.0 Hz, 1H), 6.23 (d, J=8.0 Hz, 1H), 4.54 (t, J=5.0 Hz, 2H), 4.44 (t, J=5.0 Hz, 2H), 3.75 (s, 2H). $^{13}$C NMR (101 MHz, DMSO) δ 171.13, 144.16, 143.31, 142.82, 137.02, 133.85, 130.90, 130.86, 129.08, 127.74, 125.95, 122.74, 122.31, 121.46, 120.50, 119.38, 115.74, 110.31, 63.21, 43.20, 36.75. $^{13}$C-DEPT NMR (101 MHz, DMSO) δ 144.17, 130.90, 129.09, 127.74, 125.96, 122.32, 121.46, 120.50, 119.38, 115.74, 110.31, 63.21, 43.20, 36.75.

Example 6: DPX-1-0007 (sdnX-18)

2-(2-phenyl-1H-imidazol-1-yl)ethyl 2-(2-((2,6-dichlorophenyl)amino)phenyl)acetate The required IPU: 2-(2-phenyl-1H-imidazol-1-yl)ethanol was prepared in the following way: A magnetically stirred solid mixture 2-phenylimidazole (37.7 g, 0.261 mol) and ethylene carbonate (28.8 g, 0.327 mol) in a 250 mL three necked flask round bottomed flask equipped with a bubble tube and an internal thermometer was heated in a oil bath to 130-140° C. were evolution of CO$_2$ started. The mixture was kept at this temperature until evolution of CO$_2$ ceased. More ethylenecarbonate in portions of 2-3 g was added and the mixture reheated until evolution of CO$_2$ ceased or full conversion of 2-phenylimidazole as indicated by TLC was achieved. The dark brown mixture was cooled to room temperature and dissolved in water (100 mL) and extracted with ethyl acetate (3-4×100 mL). The combined organic layers were washed with brine (100 mL) and dried over Na$_2$SO$_4$. Concentration gave a dark brown oily residue (37.7 g) which was crystallised from EtOAc-heptane to give 21.5 g of a brown solid. This material was recrystallised from EtOAc-EtOH to afford the title compound as a pale brown solid in sufficient purity to be used in subsequent steps without further purification (18.7 g, 38%).

DPX-1-0007 was subsequently prepared using an identical procedure as described for DPX-1-0001: 2-(2-phenyl-1H-imidazol-1-yl)ethanol (12 mmol, 2.26 g), Dichlofenac (6 mmol, 1.77 g), 4-Dimethylaminopyridin (0.3 mmol, 22 mg), Dicyclohexylcarbodiimid (7.2 mmol, 1.5 g) and dichloromethane (50 mL). $^1$H NMR (400 MHz, DMSO) δ 7.61-7.56 (m, 2H), 7.52 (d, J=8.1 Hz, 2H), 7.48-7.36 (m, 3H), 7.29 (d, J=1.2 Hz, 1H), 7.23-7.17 (m, 1H), 7.10-7.02 (m, 2H), 6.96 (d, J=1.2 Hz, 1H), 6.91 (s, 1H), 6.83 (td, J=7.4, 1.1 Hz, 1H), 6.23 (d, J=7.8 Hz, 1H), 4.38-4.27 (m, 4H), 3.69 (s, 2H).

Example 7: DPX-1-0008 (ALE459-3)

2-(2-propyl-1H-imidazol-1-yl)ethyl 2-(2-(2,6-dichlorophenylamino)phenyl)acetate

Using an Identical Procedure as Described for DPX-1-0001:

Dichlorfenac (6 mmol, 1.7 g), 6-(1H-imidazol-1-yl)ethan-1-ol (12 mmol, 1.8 g), Dicyclohexylcarbidiimide (7.2 mmol, 1.4 g), 4-Dimethylaminopyridine (0.6 mmol, 72 mg) and dichloromethane (50 mL) Crude yield: 3.6 g; yield after Flash Chromatography using ethyl acetate and heptanes as eluent: 1.2 g (46%). $^1$H NMR (400 MHz, DMSO-d6) δ 7.52 (d, J=8.03 Hz, 5H), 7.20 (t, J=8.03 Hz, 2H), 7.14 (dd, J=1.51, 7.53 Hz, 2H), 7.06 (dt, J=1.51, 7.78 Hz, 2H), 6.95-7.01 (m, 4H), 6.84 (dt, J=1.13, 7.47 Hz, 2H), 6.70 (d, J=1.25 Hz, 2H), 6.25 (d, J=7.78 Hz, 1H), 4.26-4.35 (m, 2H), 4.10-4.17 (m, 2H), 3.80 (s, 2H), 1.63 (dquin, J=7.28, 7.47 Hz, 2H), 0.90 (t, J=7.40 Hz, 3H). $^{13}$C NMR (400 MHz, DMSO-d6) 171.15, 147.40, 142.85, 130.92, 130.82, 129.13, 127.77, 126.48, 125.98, 122.82, 119.44, 115.81, 63.95, 43.69, 27.65, 20.85, 13.75

Example 8: DPX-1-0009 (ALE480-1)

6-(1H-imidazol-1-yl)hexyl 2-(2-(2,6-dichlorophenylamino)phenyl)acetate

Using an Identical Procedure as Described for DPX-1-0001:

Dichlorfenac (6 mmol, 1.7 g), 6-(1H-imidazol-1-yl) hexan-1-ol (6 mmol, 1.0 g) Dicyclohexylcarbidiimide (12 mmol), 4-Dimethylaminopyridine (0.6 mmol, 72 mg) dichloromethane (50 mL). Crude yield: 2.1 g; yield after Flash Chromatography using ethyl acetate and heptanes as eluent: 0.5 g (20%). $^1$H NMR (400 MHz, DMSO-d6) 7.46-7.66 (m, 5H), 7.16-7.25 (m, 3H), 7.12 (s, 2H), 7.02-7.08 (m, 3H), 6.81-6.88 (m, 3H), 6.26 (d, J=7.78 Hz, 1H), 4.03-4.08 (m, 4H), 3.89 (t, J=7.03 Hz, 3H), 3.79 (s, 2H), 1.64 (quin, J=7.28 Hz, 3H), 1.56 (ddt, J=6.78, 7.03, 7.15 Hz, 3H), 1.22-1.33 (m, 4H), 1.14-1.22 (m, 4H). $^{13}$C NMR (400 MHz, DMSO-d6) 171.53, 142.73, 137.06, 129.15, 128.28, 127.67, 125.85, 123.30, 119.15, 115.89, 64.38, 45.75, 37.10, 30.40, 27.92, 25.49, 24.74.

Example 9: DPX-1-0010 (ALE481-2)

6-(2-propyl-1H-imidazol-1-yl)hexyl 2-(2-(2,6-dichlorophenylamino)phenyl)acetate

Using an Identical Procedure as Described for DPX-1-0001:

Dichlorfenac (6 mmol, 1.4 g), 6-(2-propyl-1H-imidazol-1-yl)hexan-1-ol (6 mmol, 1.25 g), Dicyclohexylcarbidiimide (12 mmol, 2.4 g), 4-Dimethylaminopyridin (0.6 mmol, 72 mg) and dichloromethane (60 mL). Crude yield: 1.9 g; yield after Flash Chromatography using ethyl acetate and heptanes as eluent: 0.21 g (10%). $^1$H NMR (400 MHz, DMSO-d6) δ 7.52 (d, J=8.03 Hz, 1H), 7.13-7.27 (m, 1H), 6.94-7.09 (m, 2H), 6.81-6.88 (m, 1H), 6.72 (d, J=1.00 Hz, 1H), 6.27 (s, 1H), 4.06 (t, J=6.53 Hz, 2H), 3.72-3.83 (m, 3H), 1.50-1.73 (m, 4H), 1.15-1.36 (m, 3H), 0.91 (t, J=7.40 Hz, 2H). $^{13}$C NMR (400 MHz, DMSO-d6) δ 171.52, 146.91, 142.2, 137.06, 130.84, 130.52, 129.15, 127.66, 123.31, 119.10, 115.89, 64.38, 44.64, 30.35, 27.94, 27.79, 20.92, 13.75

Example 10: DPX-1-0011

2-(1-methyl-1H-imidazol-2-yl)ethyl 2-(2-((2,6-dichlorophenyl)amino)phenyl)acetate 1-Ethyl-3-(3-dimethylaminopropyl)carbodiimide-HCl (EDC-HCl) (0.661 g, 3.45 mmol) was added solid all at once to a magnetically stirred solution of diclofenac (0.888 g, 3.00 mmol), 2-(1-methyl-1H-imidazol-2-yl)ethanol (0.379 g, 3.00 mmol) and 4-Dimethylaminopyridine (19 mg, 0.15 mmol) in dry tetrahydrofuran (20 mL) cooled in an ice bath and kept under nitrogen. The reaction mixture was stirred in an ice-bath for 30 min and then at ambient. After stirring for 12 hrs at room temperature more EDC-HCl (115 mg, 0.6 mmol) was added and stirring was continued at room temperature for 72 hrs. The mixture was concentrated and the residue partitioned between 50% saturated NH$_4$Cl (25 mL) and EtOAc (60 mL). The organic layer was washed with 50% saturated NH$_4$Cl (2×25 mL), 50% saturated NaHCO$_3$ (25 mL) and brine (30 mL). The organic layer was dried over Na$_2$SO$_4$ and concentrated. Flash Chromatography using ethyl acetate and heptanes as eluent provided the title compound which crystallised from heptane as a colorless solid (196 mg). Mp. 114.5-115.2° C. (EtOAc-Heptane). $^1$H NMR (400 MHz, DMSO) δ 7.53 (d, J=8.1 Hz, 2H), 7.24-7.18 (m, 1H), 7.17 (dd, J=7.5, 1.4 Hz, 1H), 7.10 (s, 1H), 7.06 (td, J=7.8, 1.5 Hz, 1H), 6.99 (d, J=1.2 Hz, 1H), 6.83 (td, J=7.4, 1.1 Hz, 1H), 6.71 (d, J=1.2 Hz, 1H), 6.24 (d, J=7.4 Hz, 1H), 4.39 (t, J=7.0 Hz, 2H), 3.79 (s, 2H), 3.52 (s, 3H), 2.98 (t, J=7.0 Hz, 2H). $^{13}$C NMR (101 MHz, DMSO) δ 171.37, 144.11, 142.93, 137.08, 130.98, 130.94, 129.12, 127.72, 126.27, 126.03, 122.91, 121.13, 120.45, 115.63, 62.61 (CH2), 37.08 (CH2), 32.07, 25.48 (CH2). DEPT—$^{13}$C NMR (101 MHz, DMSO) δ 130.95, 129.12, 127.73, 126.27, 126.03, 121.13, 120.44, 115.62, 62.61, 37.07, 32.07, 25.48.

Example 11: DPX-1-0012

2-(2-(2-phenyl-1H-imidazol-1-yl)ethoxy)ethyl 2-(2-((2,6-dichlorophenyl)-amino)phenyl)acetate The required IPU: 2-(2-(2-phenyl-1H-imidazol-1-yl)ethoxy)ethanol was obtained as a byproduct in the synthesis of another IPU: 2-(2-phenyl-1H-imidazol-1-yl)ethanol (see under DPX-1-0007) in the following way: The filtrate from the initial crystallisation was purified by Flash Chromatography using EtOAc:heptane→EtOAc:MeOH as eluent and fractions containing the title compound was combined (~7 g) and recrystallised from EtOAc:heptane to give 4.56 g of pale yellow solid. This material was purified again by Flash Chromatography using EtOAc→EtOAc:MeOH (90:10) as eluent. Relevant fractions were combined and recrystallised from toluene to afford the title compound as a colourless solid (1.39 g, 2.3%). Mp. 94.4-95.1° C. (toluene). $^1$H NMR (400 MHz, DMSO) δ 7.66-7.62 (m, 2H), 7.51-7.41 (m, 3H), 7.38 (d, J=1.0 Hz, 1H), 7.00 (d, J=1.0 Hz, 1H), 4.59 (t, J=5.5 Hz, 1H), 4.17 (t, J=5.5 Hz, 2H), 3.72 (t, J=5.5 Hz, 2H), 3.49-3.42 (m, 2H), 3.40-3.35 (m, 2H). $^{13}$C NMR (101 MHz, CDCl$_3$) δ 148.19, 130.91, 129.23, 128.91, 128.72, 128.70, 121.06, 72.68, 70.58, 61.71, 46.73.

Subsequently, DPX-1-0012 was prepared in the following way: 1-Ethyl-3-(3-dimethylaminopropyl)carbodiimide-HCl (EDC-HCl) (551 mg, 2.87 mmol) was added solid all at once to a magnetically stirred solution of Diclofenac (741 mg, 2.50 mmol), 2-(2-(2-phenyl-1H-imidazol-1-yl)ethoxy)ethanol (581 mg, 2.50 mmol) and 4-Dimethylaminopyridine (16 mg, 0.13 mmol) in dry tetrahydrofuran (15 mL) cooled in an ice bath and kept under nitrogen. The reaction mixture was stirred in an ice bath for 30 min and then at ambient temperature. After stirring for 12 hours more EDC-HCl (96 mg, 0.5 mmol) was added and stirring was continued at room temperature for 72 hours. The mixture was concentrated and the residue partitioned between 50% saturated NH$_4$Cl (25 mL) and EtOAc (50 mL). The organic layer was washed with 50% saturated NH$_4$Cl (2×25 mL), 50% saturated NaHCO$_3$ (25 mL) and brine (30 mL). The organic layer was dried over Na$_2$SO$_4$ and concentrated. The residue was purified by Flash Chromatography using ethyl acetate and heptanes as eluent to afford the title compound (274 mg) as thick pale yellow oil. $^1$H NMR (400 MHz, DMSO) δ 7.64-7.59 (m, 2H), 7.52 (d, J=8.1 Hz, 2H), 7.48-7.37 (m, 3H), 7.30 (d, J=1.2 Hz, 1H), 7.23-7.18 (m, 1H), 7.16 (dd, J=7.6, 1.4 Hz, 1H), 7.07-7.01 (m, 2H), 6.98 (d, J=1.2 Hz, 1H), 6.82 (td, J=7.4, 1.1 Hz, 1H), 6.25 (d, J=7.8 Hz, 1H), 4.17-4.09 (m, 4H), 3.78 (s, 2H), 3.69 (t, J=5.3 Hz, 2H), 3.59-3.54 (m, 2H). $^{13}$C NMR (101 MHz, DMSO) δ 171.45, 146.93, 142.81, 137.08, 130.92, 130.85, 130.63, 129.14, 128.78, 128.38, 128.30, 127.86, 127.71, 125.88, 123.12, 121.44, 120.62, 115.89, 69.61, 68.18, 63.75, 46.00, 36.94. DEPT $^{13}$C NMR (101 MHz, DMSO) δ 130.85, 129.13, 128.78, 128.38, 128.30, 127.86, 127.71, 125.88, 121.44, 120.62, 115.89, 69.60 (CH2), 68.18 (CH2), 63.75 (CH2), 46.00 (CH2), 36.94 (CH2).

Example 12: DPX-2-0001 (ALE 406)

4-(dimethylamino)phenethyl 2-(6-methoxynaphthalen-2-yl)propanoate 2-(6-methoxynaphthalen-2-yl)propanoyl chloride (acid chloride of Naproxen) (1 g, 4 mmol) was dissolved in dichloromethane (20 mL) and pyridine (30 mL) was added, and finally a solution of the 2-(4-(dimethylamino)phenyl)ethanol (0.64 g, 4 mmol) in dichloromethane (10 mL) was added. The mixture was left over night under stirring at room temperature. After addition of dichloromethane the reaction mixture was washed with first a saturated bicarbonate solution (100 mL) and second water (100 mL). The organic phase was dried and concentrated to yield an oily residue. The crude product was purified by vacuum liquid chromatography on silica (20-45 µm) using heptane (60 mL) followed by heptane-ethyl acetate (4:1 v/v) as eluent. Yield 0.52 g (35%). $^1$H NMR (300 MHz, CDCl$_3$): δ 7.70-7.64 (3H, m); 7.37 (1H, dd, J=6.60; 1.5 Hz); 7.15-7.11 (2H, m); 6.9 (2H, d, J=8.8 Hz); 6.52 (2H, d, J=8.56); 4.27 (2H, t, J=6.88 Hz); 3.92 (3H,$); 3.84 (1H, q, J=7.15 Hz); 2.88 (6H, s); 2.76 (2H, t, J=7.15 Hz); 1.57 (3H, d, J=7.15 Hz). 13C NMR (400 MHz, DMSO-d6) δ 173.76, 157.18, 135.60, 135.60, 129.24, 126.96, 126.23, 125.73, 118.66, 105.69, 65.29, 55.15, 44.51, 33.30, 18.17.

Example 13: DPX-2-0002 (ALE 412)

2-(methyl(phenyl)amino)ethyl 2-(6-methoxynaphthalen-2-yl)propanoate

Using an identical procedure as described for DPX-2-0001 using 2-(6-methoxynaphthalen-2-yl)propanoyl chloride (1.7 g, 7.2 mmol) and 2-(methyl(phenyl)amino)ethanol (1.10 g, 7.2 mmol). Yield 0.9 g (36%). $^1$H NMR (300 MHz, CDCl$_3$): δ 7.7 (3H, d, J=8.53 Hz); 7.62 (1H, d, J=1.38 Hz); 7.35 (1H, dd, J=8; 1.65 Hz); 7.22-7.10 (2H, m), 6.69 (3H, m); 4.23 (2H, t, J=5.78); 3.92 (3H, s); 3.80 (1H, q, J=7.15 Hz); 3.53 (2H, t, J=5.78 Hz); 2.83 (3H, s); 1.54 (3H, d, J=6.88 Hz). $^{13}$C NMR (400 MHz, DMSO-d6) δ 173.87, 157.17, 135.53, 133.31, 128.92, 126.94, 126.64, 118.71, 115.88, 111.91, 105.70, 61.80, 55.14, 50.18, 44.50, 38.06, 18.22.

Example 14: DPX-2-0003 (ALE 416)

3-(methyl(phenyl)amino)propyl 2-(6-methoxynaphthalen-2-yl)propanoate

Using an identical procedure as described for DPX-2-0001 using 2-(6-methoxynaphthalen-2-yl)propanoyl chloride (1.7 g, 7.14 mmol) and 3-(methyl(phenyl)amino)propan-1-ol (1.19 g; 7.14 mmol). Yield 1.75 g (64%). $^1$H NMR (300 MHz, CDCl$_3$): δ 7.72-7.68 (3H, m); 7.41 (1H, dd, J=6.60 Hz; 1.93 Hz); 7.17-7.10 (3H, m); 7.71-7.53 (2H, m); 4.14 (2H, t, J=6.60 Hz); 3.92 (3H, s); 3.86 (2H, t, J=7.15 Hz); 3.28-3.19 (2H, m); 3.75 (3H, s); 1.84-1.78 (2H, m) 1.605 (3H, d, J=7.15 Hz). $^{13}$C NMR (400 MHz, DMSO-d6) δ 173.84, 157.19, 148.73, 135.71, 133.34, 128.88, 126.99, 125.64, 118.75, 115.56, 111.79, 105.75, 62.10, 55.15, 48.14, 44.48, 37.55, 25.17, 18.13.

Example 15: DPX-2-0004 (sdnX9)

2-(pyridin-2-yl)ethyl 2-(6-methoxynaphthalen-2-yl)propanoate

Using an Identical Procedure as Described for DPX-1-0001:

2-(pyridin-2-yl)ethanol (8.12 mmol, 1.00 g), Naproxen (8.93 mmol, 2.06 g), Dimethylaminopyridin (0.4 mmol, 50 mg), 1-Ethyl-3-(3-dimethylaminopropyl) carbodiimide-HCl (EDC-HCl) (12.18 mmol, 2.33 g), Acetonitrile (5 mL) and Dimethylformamide (3 mL). Crude yield: 4.3 g. The oil was purified by flash chromatography using ethyl acetate and heptanes as eluent to give a colorless oil. The pure oil was dissolved in diethyl ether (50 mL) and 2M HCl in diethyl ether (500 uL) was added. After drying under oil pump vacuum, white crystals precipitated. $^1$H (CDCl$_3$) 1.52 (d, 2H), 3.02 (t, 2H), 3.91-3.95 (m, 3H), 3.98 (s, 3H), 4.36-4.41 (m, 2H), 6.60 (d, 1H), 7.00-7.04 (m, 1H), 7.12-7.19 (m, 2H), 7.24-7.29 (m, 1H), 7.45 (dd, 1H), 7.60 (s, 1H), 7.16-7.20 (m, 2H), 8.46-8.49 (m, 1H). $^{13}$C (CDCl$_3$) 105.53, 118.86, 121.35, 123.32, 125.95, 126.19, 127.02, 128.88, 129.25, 133.63, 135.62, 136.03, 149.26, 157.60, 157.84, 174.39.

Example 16: DPX-2-0005 (JBX019)

2-(1H-benzo[d]imidazol-1-yl)ethyl 2-(6-methoxynaphthalen-2-yl)propanoate

1-Ethyl-3-(3-dimethylaminopropyl)carbodiimide-HCl (EDC-HCl) (2.20 g, 11.5 mmol) was added solid all at once to a magnetically stirred solution of naproxen (2.30 g, 10.0 mmol), 1-(2-hydroxyethyl)imidazole (1.12 g, 10.0 mmol) and 4-Dimethylaminopyridine (61 mg, 0.5 mmol) in dry tetrahydrofuran (50 mL) cooled in an ice bath and kept under nitrogen. The reaction mixture was stirred in an ice bath for 30 min and at ambient temperature. More EDC-HCl (400 mg, 2 mmol) was added after 13 hrs, 17 hrs. After stirring for 22 hrs at room temperature the mixture was concentrated and the residue partitioned between water (50 mL), saturated NH$_4$Cl (20 mL) and EtOAc (120 mL). The organic layer was washed with 50% saturated NH$_4$Cl (2×50 mL), 50% saturated NaHCO$_3$ (50 mL) and brine (50 mL). The organic layer was dried and concentrated. The oily residue was purified by Flash Chromatography using ethyl acetate and heptanes as eluent afforded a colourless oil (2.74 g, 84%) after drying in high vacuum. The oil was crystallised from ether and recrystallised from Tert-butylmethylether (~20 mL, seeded) to afford the title compound as a colourless solid (2.21 g, 68.3%). Mp. 60.6-61.3° C. $^1$H NMR (400 MHz, DMSO) δ 7.80 (d, J=9.0 Hz, 1H), 7.77 (d, J=8.5 Hz, 1H), 7.68 (d, J=1 Hz, 1H), 7.51 (s, 1H), 7.33 (dt, J=5.5, 3 Hz, 1H), 7.30 (d, J=2.5 Hz, 1H), 7.17 (dd, J=9, 2.5 Hz, 1H), 6.98 (t, J=1 Hz, 1H), 6.78 (t, J=1 Hz, 1H), 4.34-4.12 (m, 4H), 3.92 (q, J=7 Hz, 1H), 3.88 (s, 3H), 1.45 (d, J=7 Hz, 3H). $^{13}$C NMR (101 MHz, DMSO) δ 173.52, 157.19, 137.40, 135.30, 133.33, 129.15, 128.37, 128.25, 126.99, 126.20, 125.63, 119.46, 118.73, 105.69, 63.74, 55.15, 44.94, 44.35, 18.19.

Example 17: DPX-2-0006 (JBX017)

2-(1H-benzo[d]imidazol-1-yl)ethyl 2-(6-methoxynaphthalen-2-yl)propanoate

1-Ethyl-3-(3-dimethylaminopropyl)carbodiimide-HCl (EDC-HCl) (2.20 g, 11.5 mmol) was added solid all at once to a magnetically stirred solution of naproxen (2.30 g, 10.0 mmol), 2-(1H-benzo[d]imidazol-1-yl)ethanol (1.62 g, 10.0 mmol) and 4-Dimethylaminopyridine (68 mg, 0.5 mmol) in dry tetrahydronfuran (50 mL) cooled in an ice bath and kept under nitrogen. The reaction mixture (slurry—EDC-HCl failed to dissolve) was stirred in an ice bath for 30 min and at ambient temperature. More EDC-HCl (400 mg, 2 mmol) was added after 3, 5 and 6 hours. After stirring for 48 hours the mixture was concentrated and the residue partitioned between water (50 mL), saturated NH$_4$Cl (20 mL) and EtOAc (120 mL). The organic layer was washed with 50% saturated NH$_4$Cl (2×50 mL), 50% saturated NaHCO$_3$ (50 mL) and brine (50 mL). The organic layer was dried and concentrated. Flash Chromatography using ethyl acetate and heptanes as eluent afforded the title compound as a colourless solid (3.33 g, 88.8% yield). Mp. 125.0-125.7° C. $^1$H NMR (400 MHz, DMSO) δ 8.09 (s, 1H), 7.75 (d, J=9.0 Hz, 1H), 7.71 (d, J=8.5 Hz, 1H), 7.69-7.63 (m, 1H), 7.61-7.54 (m, 2H), 7.28 (d, J=2.5 Hz, 1H), 7.26-7.18 (m, 3H), 7.16 (dd, J=9, 2.5 Hz, 1H), 4.58-4.32 (m, 4H), 3.87 (s, 3H), 3.83 (q, J=7 Hz, 1H), 1.37 (d, J=7 Hz, 3H). $^{13}$C NMR (101 MHz, DMSO) δ 173.52, 157.18, 144.13, 143.29, 135.19, 133.83, 133.29, 129.13, 128.32, 126.93, 126.09, 125.58, 122.25, 121.46, 119.38, 118.69, 110.37, 105.67, 63.03, 55.15, 44.36, 43.10, 18.12. DEPT $^{13}$C NMR (101 MHz, DMSO) δ 144.12, 129.13, 126.93, 126.09, 125.58, 122.25, 121.45, 119.37, 118.69, 110.36, 105.67, 63.03 (CH2), 55.14, 44.36, 43.10 (CH2), 18.12.

Example 18: DPX-2-0007 (JBX018)

2-(2-phenyl-1H-imidazol-1-yl)ethyl 2-(6-methoxynaphthalen-2-yl)propanoate

1-Ethyl-3-(3-dimethylaminopropyl)carbodiimide-HCl (EDC-HCl) (2.20 g, 11.5 mmol) was added solid all at once to a magnetically stirred solution of naproxen (2.30 g, 10.0 mmol), (1.88 g, 10.0 mmol) and 4-Dimethylaminopyridine (61 mg, 0.5 mmol) in dry tetrahydrofuran (50 mL) cooled in an ice bath and kept under nitrogen. The reaction mixture (slurry—EDC-HCl failed to dissolve) was stirred in an ice bath for 30 min and at ambient temperature. More EDC-HCl (400 mg, 2 mmol) was added after 13 hrs and 17 hrs. After stirring for 22 hours at room temperature full conversion of naproxen was obtained. The mixture was concentrated and the residue partitioned between water (50 mL), saturated NH$_4$Cl (20 mL) and EtOAc (120 mL). The organic layer was washed with 50% saturated NH$_4$Cl (2×50 mL), 50% saturated NaHCO$_3$ (50 mL) and brine (50 mL). The organic layer was dried and concentrated. Flash Chromatography using ethyl acetate and heptanes as eluent afforded the title compound as a pale yellow oil. $^1$H NMR (400 MHz, DMSO) δ 7.77 (d, J=9.0 Hz, 1H), 7.74 (d, J=8.6 Hz, 1H), 7.61 (d, J=1.4 Hz, 1H), 7.58-7.51 (m, 2H), 7.45-7.38 (m, 3H), 7.29 (d, J=2.5 Hz, 1H), 7.24 (dd, J=8.5, 1.8 Hz, 1H), 7.19-7.13 (m, 2H), 6.90 (d, J=1.2 Hz, 1H), 4.37-4.20 (m, 4H), 3.86 (s, 3H), 3.77 (q, J=7.1 Hz, 1H), 1.36 (d, J=7.1 Hz, 3H).

HCl-salt of DPX-2-0007: 571 mg of this oil was dissolved in a mixture of dry ether (20 mL) and dry tetrahydrofuran (10 mL) under nitrogen at 0° C. 2M HCl in ether (4 mL, 8 mmol) was added drop wise by syringe resulting in the formation a sticky gum. The solvent was decanted off and the gum was washed with dry ether (20 mL). The gum was dried in high vacuum and then crystallised by dissolving it in ethanol (2 mL) and slowly adding dry diethyl ether until no more solid formed. The free flowing solid was dried in vacuum to afford the title compound (452 mg) as an off white solid. Mp. 188.5-189.6° C. (ethanol/ether). $^1$H NMR (400 MHz, DMSO) δ 15.29 (br s, 1H), 7.85 (d, J=2.0 Hz, 1H), 7.80-7.71 (m, 3H), 7.69-7.64 (m, 1H), 7.63-7.53 (m, 5H), 7.30 (d, J=2.5 Hz, 1H), 7.21-7.15 (m, 2H), 4.46-4.35 (m, 4H), 3.88 (s, 3H), 3.81 (q, J=7.0 Hz, 1H), 1.37 (d, J=7.0 Hz, 3H). $^{13}$C NMR (101 MHz, DMSO) δ 173.46, 157.20, 144.42, 135.15, 133.30, 131.88, 129.71, 129.15, 129.06, 128.32, 127.06, 125.81, 125.55, 122.90, 122.34, 119.58, 118.82, 105.77, 62.28, 55.18, 46.50, 44.11, 18.15. DEPT $^{13}$C NMR (101 MHz, DMSO) δ 131.88, 129.71, 129.15, 129.06, 127.06, 125.82, 125.56, 122.90, 119.59, 118.82, 105.77, 62.28 (CH2), 55.18, 46.50 (CH2), 44.11, 18.15.

Example 19—Dissolution of Prodrug in Synovial Fluid Followed by Formation of the Active Agent The stability of a suspension of a prodrug according to the invention in 80% human synovial fluid pH 7.4 (SF) from arthritis patients can be investigated at 37° C. The reaction is initiated by adding 5 ml preheated SF to 2 mg prodrug. At appropriate time intervals, 400 µl samples are taken and centrifuged for 5 min at 13.000 rpm and 200 µl of the supernatant is deproteinised with 400 µl acetonitrile. After centrifugation for 4 min at 13000 rpm, the supernatant is analysed by HPLC for prodrug as well as formed drug.

Example 20—Preliminary Precipitation Experiment, No Esterases Present

A concentrated solution of a prodrug according to the invention in 0.01 M HCl is prepared by adding 0.2 ml of 1×10$^{-5}$M methanol solution of DPX-4-0001 to 1.0 ml 0.01 M HCl resulting in a final concentration of 1.7×10$^{-4}$M. After addition of 300 µl of this solution (0.02 mg) to 5 ml 67 mM phosphate buffer pH 7.4, a precipitation process is expected. At appropriate time intervals, samples are withdrawn and centrifuged for 5 min at 13.000 rpm and the supernatant is analysed by HPLC for prodrug and formed drug.

Example 21—Solubility of DPX-2-0007 (JBX018) at pH 3.4 and Precipitation in Buffer pH 7.4

A suspension of DPX-2-0007 (as hydrochloride salt) was formed by adding 30 mg to 4 mL demineralized water. After rotation of the suspension at 37° C. for 3 days, 1.0 mL sample was taken and after filtration (disposable syringe filters), the solution was diluted in methanol:water 1:1 and analyzed immediately by HPLC for prodrug. Quantitation of DPX-2-0007 was done from peak area measurements in relations to those of standards analysed by HPLC at the same conditions. The pH in the solution was measured to 3.40. The following HPLC method was used: Merck Hitachi L 6200 pump connected to Merck Hitachi 4250 UV detector. Reversed phase chromatography was performed using a RP 18 Symmetry Shields® column (150×4.6 mm, 5 µm particles) equipped with a SecurityGuard precolumn (Phenomenex, Torrance, Calif., USA). The flow rate was set at 1 mL/min and the column effluent was monitored at 230 nm. The mobile phase consisted of 35% (v/v) acetonitrile and 65% (v/v) of 0.1% (v/v) phosphoric acid pH 3.2. The retention time of naproxen and DPX-2-0007 were 19 and 5.8 min, respectively.

The solubility of DPX-2-0007 at pH 3.4 was determined to 6.8±0.6 mg/mL. Thus, a 1000-fold increase in the solubility compared to the solubility of DPX-2-0007 in buffer pH 7.4 (PBS—see Table 1).

TABLE 1

Solubilities of the prodrugs ($S_{prodrug}$) in PBS (67 mM phosphate buffer pH 7.4), the apparent pseudo-zero-order rate constant ($k_0$) and the estimated pseudo first-order rate constant ($k_{hyd}$) for cleavage of the prodrugs in PBS and half-lives ($t_{1/2}$) for hydrolysis of the prodrugs in 80% human plasma at 37° C.

| Prodrug | $S_{prodrug}$ ± SD | | $k_0$ | $k_{hyd}$ | $t_{1/2\ in\ PBS}$ | $t_{1/2\ in\ plasma}$ |
| | µg/mL | mM | M/day | day$^{-1}$ | day | min |
|---|---|---|---|---|---|---|
| DPX-1-0001 | 0.01 | 2 × 10$^{-5}$ | | | | |
| DPX-1-0002 | <0.1 | <0.0002 | | | | |
| DPX-1-0004 | 3 ± 1 | 0.007 ± 0.001 | 1.1 × 10$^{-6}$ | 1.5 × 10$^{-1}$ | 5 | 25 |
| DPX-1-0005 | 1 | 0.003 | | | | |

TABLE 1-continued

Solubilities of the prodrugs ($S_{prodrug}$) in PBS (67 mM phosphate buffer pH 7.4), the apparent pseudo-zero-order rate constant ($k_0$) and the estimated pseudo first-order rate constant ($k_{hyd}$) for cleavage of the prodrugs in PBS and half-lives ($t_{1/2}$) for hydrolysis of the prodrugs in 80% human plasma at 37° C.

| Prodrug | $S_{prodrug}$ ± SD µg/mL | mM | $k_0$ M/day | $k_{hyd}$ day$^{-1}$ | $t_{1/2\ in\ PBS}$ day | $t_{1/2\ in\ plasma}$ min |
|---|---|---|---|---|---|---|
| DPX-1-0006 | 7 ± 2 | 0.015 ± 0.004 | $2.4 \times 10^{-6}$ | $1.7 \times 10^{-1}$ | 4 | 3 |
| DPX-1-0007 | 43 ± 2 | 0.086 ± 0.003 | $2.5 \times 10^{-7}$ | $2.9 \times 10^{-3}$ | 242 | 49 |
| DPX-1-0008 | 0.3 | 0.0007 | | | | |
| DPX-1-0009 | <0.3 | <0.0007 | | | | |
| DPX-1-0010 | <0.4 | <0.0008 | | | | |
| DPX-1-0011 | 0.1 | 0.0002 | | | | |
| DPX-1-0012 | <0.3 | <0.0006 | | | | |
| DPX-2-0001 | <0.3 | <0.0008 | | | | |
| DPX-2-0002 | <0.2 | <0.0006 | | | | |
| DPX-2-0003 | <1 | <0.003 | | | | |
| DPX-2-0004 | 19 ± 1 | 0.052 ± 0.002 | $1.7 \times 10^{-6}$ | $3.3 \times 10^{-2}$ | 21 | 287 |
| DPX-2-0005 | 146 ± 5 | 0.45 ± 0.02 | | | | 64 |
| DPX-2-0006 | 5 ± 1 | 0.015 ± 0.002 | $1.0 \times 10^{-6}$ | $6.6 \times 10^{-2}$ | 11 | 511 |
| DPX-2-0007 | 7 ± 1 | 0.016 ± 0.001 | $1.0 \times 10^{-6}$ | $6.5 \times 10^{-2}$ | 11 | 62 |

Upon addition of 1.0 mL of the concentrated aqueous solution of DPX-2-0007 at pH 3.4 to 1.0 mL 67 mM phosphate buffer pH 7.4, a precipitation was immediately observed. The pH in the suspension was measured to 7.0.

Example 22—Solubility of DPX-2-0006 at pH 3 in the Presence of N,N-dimethyl acetamide (DMA)

A suspension of DPX-2-0006 was formed by adding 10 mg to 3 mL demineralized water, 0.05 mL 0.100 M HCl was added to obtain a pH of 3. After rotation of the suspension at 37° C. for 1 days, 0.5 mL sample was taken and after filtration (disposable syringe filters), the solution was diluted in methanol:water 1:1 and analyzed immediately by HPLC for prodrug. Quantitation of DPX-2-0006 was done from peak area measurements in relations to those of standards analysed by HPLC at the same conditions. The HPLC method described in Example 29 was applied and the retention time of DPX-2-0006 was 14 min, respectively. N,N-dimethylacetamide (DMA) was added stepwise to the acidic suspension of DPX-2-0006 and the amount of DPX-2-0006 dissolved in the presence of various volumes of DMA was determined after 1-3 days rotation at 37° C. as described above.

The solubility of DPX-2-0006 at pH 2.9 was 0.18 mg/ml. In the presence of 5%, 15%, 30% and 50% (v/v) DMA, the solubility was increased to 0.25, 0.35, 0.57 and 2.25 mg/ml, respectively.

Example 23—Determination of Solubilities and Stabilities of the Prodrugs in Buffer pH 7.4

Suspensions of the prodrugs in 67 mM phosphate buffer pH 7.4 (PBS) were prepared by adding 10 mL PBS to approximately 5 mg prodrug. The suspensions were kept unstirred at 37° C. in an incubator hood. At appropriate time intervals over 23 days, about 500 µL samples were taken and after filtration (disposable syringe filters), the solutions were analyzed immediately by HPLC for parent drug and remaining prodrug. Quantitation of parent drug and prodrug was done from peak area measurements in relations to those of standards analysed by HPLC at the same conditions. For the naproxen prodrug, the HPLC method described in example 29 were applied. For the diclofenac and ibuprofen prodrugs, the following method was used: Merck Hitachi L 6000 pump connected to Merck Hitachi 4250 UV detector. Reversed phase chromatography was performed using a C18 Gemini® RP column (150×4.6 mm, 5 µm particles) (Phenomenex, Torrance, Calif., USA) equipped with a SecurityGuard pre-column (Phenomenex, Torrance, Calif., USA). The flow rate was set at 1 mL/min and the column effluent was monitored at 230 nm. The mobile phase consisted of 35% (v/v) acetonitrile and 65% (v/v) of 0.1% (v/v) phosphoric acid pH 3.2. The retention times varied in the range of 3 to 30 min.

From the observed relatively stable concentration of dissolved prodrugs measured in the suspensions after 8-9 day up to 23 days, the solubilities of the prodrugs ($S_{prodrug}$) were determined. In this time interval, the rate of appearance of parent drug was determined and an apparent pseudo-zero-order rate constant ($k_0$) was obtained. By assuming that the dissolution rates were much faster than the conversion of the prodrugs to the parent drug, pseudo first-order rate constants ($k_{hyd}$) for cleavage of the prodrugs were calculated according to:

$$-\frac{d[\text{Prodrug}]}{dt} = \frac{d[\text{Drug}]}{dt} = k_{hyd} S_{prodrug} = k_0$$

All data are summarized in Table 1.

Example 24—Hydrolysis of the Prodrugs in 80% Human Plasma

At 37±0.5° C., the hydrolysis rate of the prodrugs was measured in 80% human plasma. An appropriate aliquot (20-100 µL) of 1 mg/ml prodrug solution in methanol was transferred to 5.0 ml of preheated plasma. At appropriate time intervals, 300 µl sample aliquots were withdrawn and transferred to 600 µl acetonitrile and mixed thoroughly. After centrifugation at 13500 rpm for 5 min, the supernatant was analyzed by HPLC for parent drug and remaining prodrug. The HPLC methods described in Example 29 and 31 were applied.

The half-lives for cleavage of the prodrugs in 80% human plasma were in the range 3-755 min (DPX-3-0006 remained intact after incubation in plasma for 10 h).

REFERENCES

Ref. 1: Reuben et al.
Reuben S. S., Connelly N. R. (1995) Postoperative analgesia for outpatient arthroscopic knee surgery with intraarticular bupivacaine and ketorolac. Anesth Analg 80: 1154-1157

Ref. 2: Rasmussen et al.
Rasmussen S., Larsen A. S., Thomsen S. T., Kehlet H. (1998) Intra-articular glucocorticoid, bupivacaine and morphine reduces pain, inflammatory response and convalescence after arthroscopic meniscectomy. Pain 78: 131-134

Ref. 3: R. Williams
pKa Data Compiled by R. Williams (downloadable from http://research.chem.psu.edu/brpgroup/pKa_compilation.pdf)

Ref. 4: Caballero et al.
Caballero et al. (2006) "Theoretical prediction of relative and absolute pKa values of aminopyridines", Biophysical Chemistry 124(2), p 155-160 (Ref. 3).

Ref. 5: Drustrup et al.
Drustrup et al. (1991) "Utilization of prodrugs to enhance the transdermal absorption of morphine", International Journal of Pharmaceutics 71, 105-116

The invention claimed is:
1. A prodrug of diclofenac or naproxen of formula:

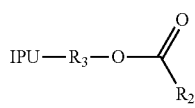

or salts, solvates or hydrates thereof;
wherein:
IPU is an Immobility-Promoting Unit comprising a substituted or unsubstituted imidazolyl group, and the IPU has a pKa between 4 and 8.4 at 37° C. in phosphate buffered saline;
$R_2$ is an acyloxy residue of diclofenac or naproxen;
$R_3$ is selected from the following structures for HO-$R_3$-IPU:

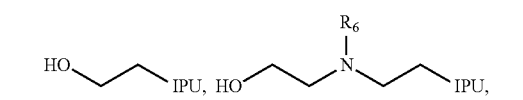

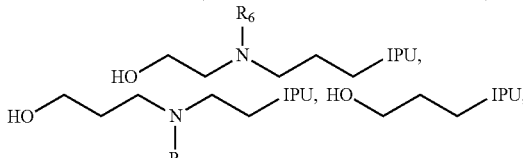

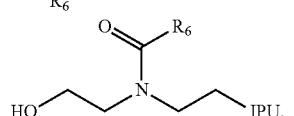

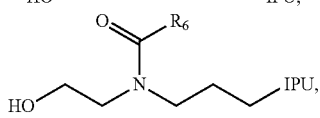

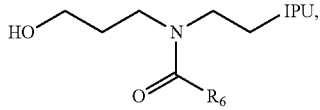

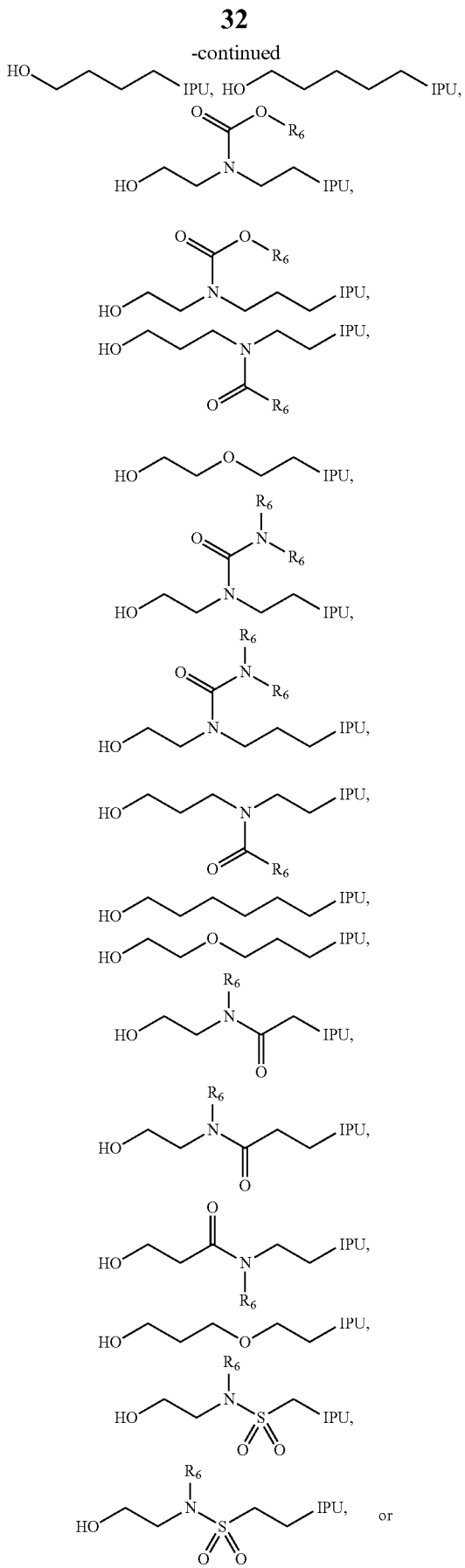

-continued
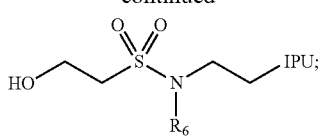
wherein $R_6$ is H or $CH_3$; and
$R_4$ and $R_5$ are independently selected from the group consisting of:
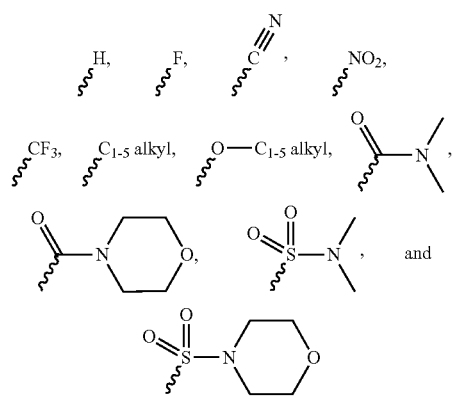
wherein the prodrug of diclofenac or naproxen according to the formula is selected from the following structures:
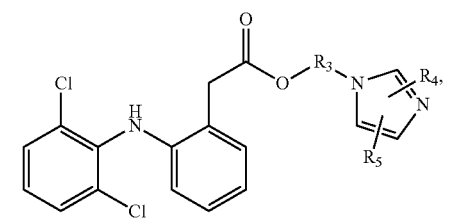
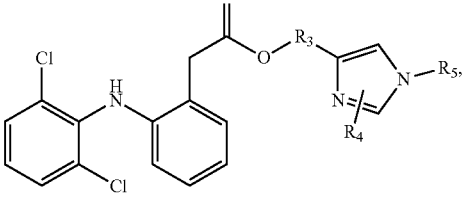
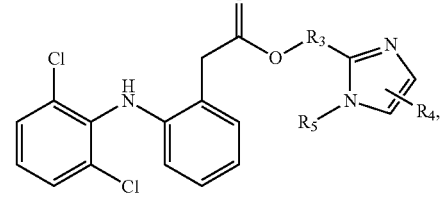
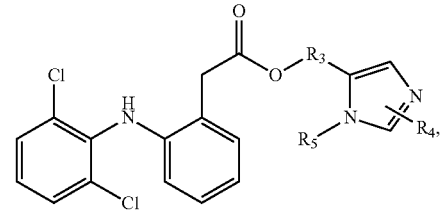
-continued
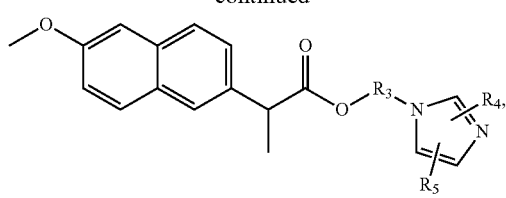
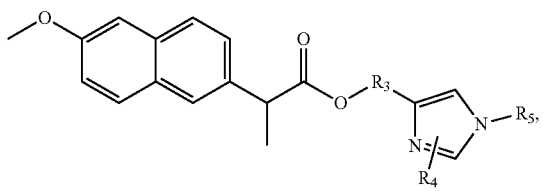
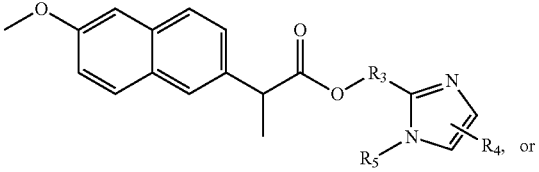
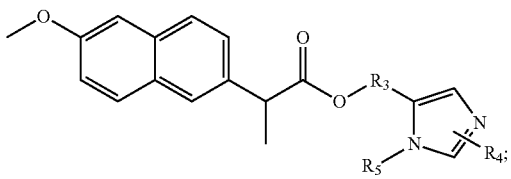
or salts, solvates or hydrates thereof.
2. The prodrug, according to claim 1, selected from the following structures:
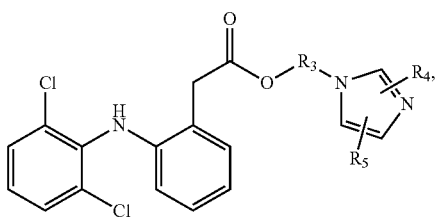
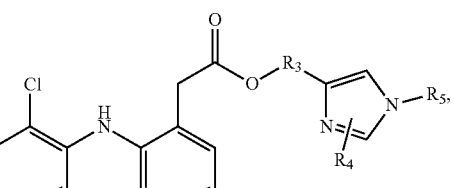
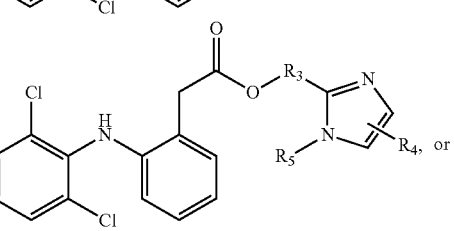

or salts, solvates or hydrates thereof.

3. The prodrug according to claim 1, selected from the following structures:

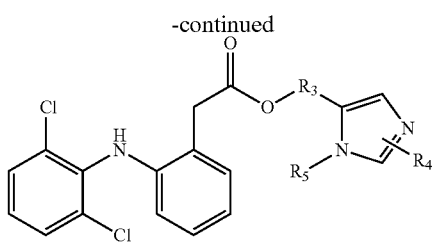

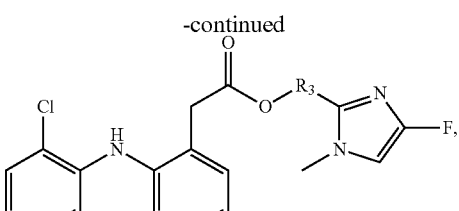

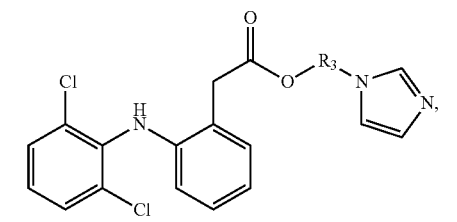

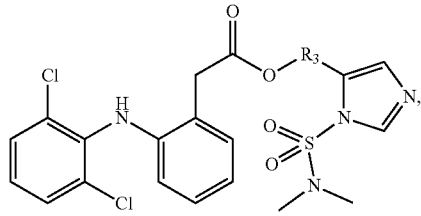

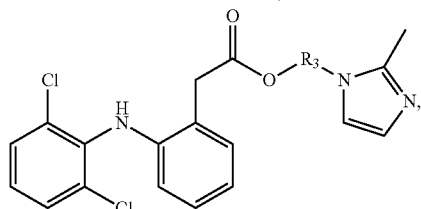

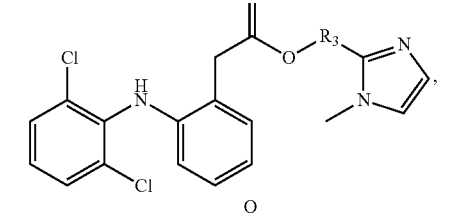

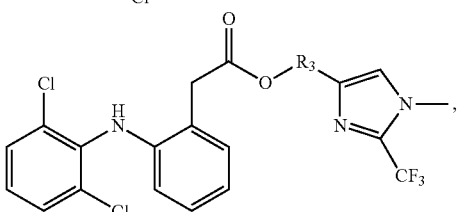

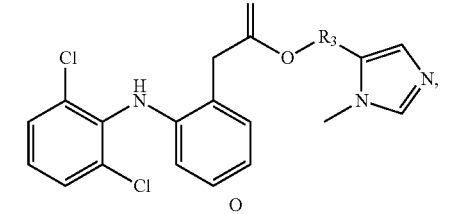

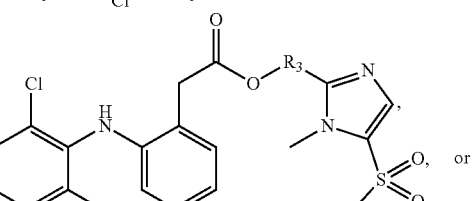

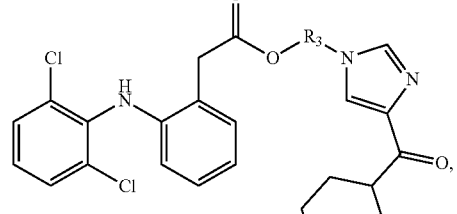

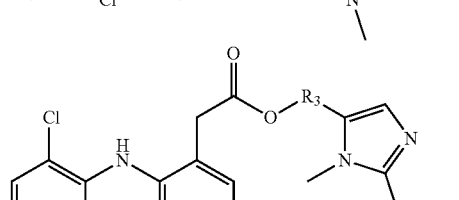 or

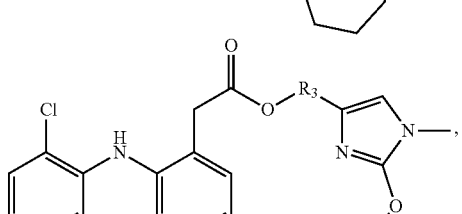

or salts, solvates or hydrates thereof.

4. A pharmaceutical composition, comprising a therapeutically effective amount of the prodrug according to claim 1, and at least one pharmaceutically acceptable carrier, vehicle or adjuvant.

5. A pharmaceutical composition according to claim 4, wherein the composition is suitable for intra-articular injection.

6. A pharmaceutical composition, comprising a therapeutically effective amount of the prodrug according to claim 3, and at least one pharmaceutically acceptable carrier, vehicle or adjuvant.

7. The pharmaceutical composition according to claim 6, wherein the composition is suitable for intra-articular injection.

8. A method of treating postoperative pain, comprising administering the prodrug according to claim 1 to a subject in need thereof.

9. The method according to claim 8, wherein the postoperative pain is postoperative pain following arthroscopic surgery.

10. The method according to claim 9, further comprising administering one or more local anaesthetic agents selected from the group consisting of amethocine, chlorprocaine, etidocaine, lidocaine, bupivacaine, mepivacaine, prilocaine, ropivacaine, and procaine.

11. The method according to claim 9, further comprising administering one or more opioid or strong analgesics selected from the group consisting of alfentanil, alphaprodine, anilerdine, buprenorphine, buturphenol, codeine, dextromoramide, dextroproproxyphene, dihydrocodeine, fentanyl, dydrocodone, hydromorphone, ketobemidone, meptazinol, methadone, morphine, oxycodone, oxymorphone, pentazocine, pethidine, phenazocine, phenoperidine, and sulfentanil.

12. A method of treating inflammation, comprising administering the prodrug according to claim 1 to a subject in need thereof.

13. A method of treating postoperative pain, comprising administering the prodrug according to claim 3 to a subject in need thereof.

14. The method according to claim 13, wherein the postoperative pain is postoperative pain following arthroscopic surgery.

15. A method of treating inflammation, comprising administering the prodrug according to claim 3 to a subject in need thereof.

16. An intra-articular injection comprising a prodrug according to claim 1, wherein the composition is in the form of an aqueous solution having a pH of from 1.5 to 5, from which the compound of formula I precipitates in the joint, at least partly, after administration.

17. The intra-articular injection according to claim 16, wherein the prodrug is according to claim 3 selected from the following structures:

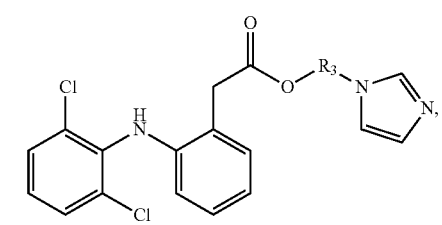

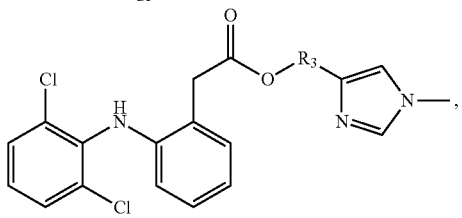

-continued

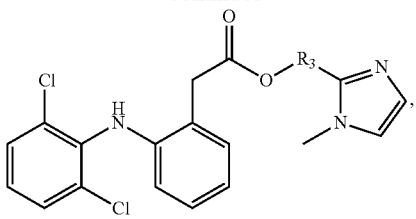

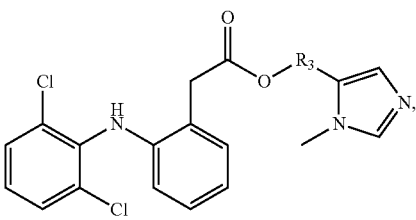

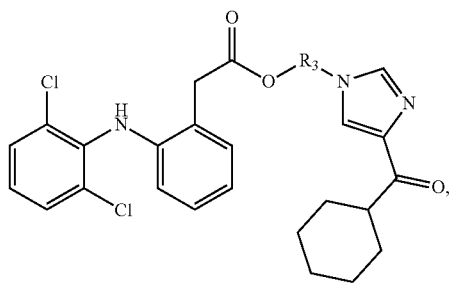

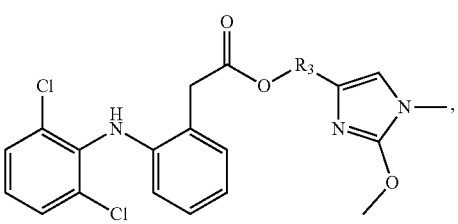

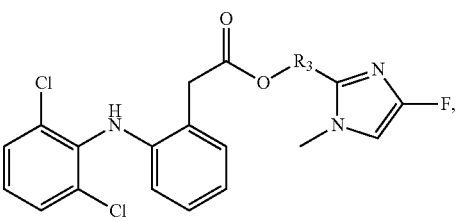

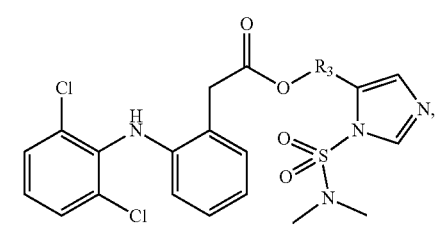

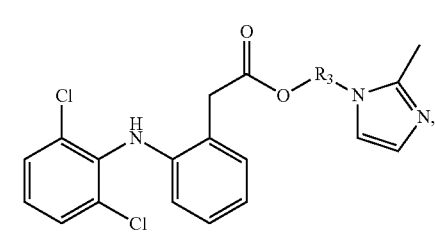

-continued
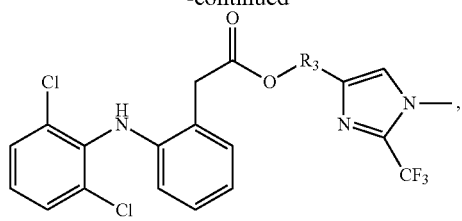
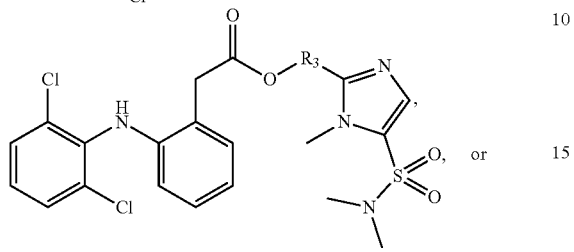
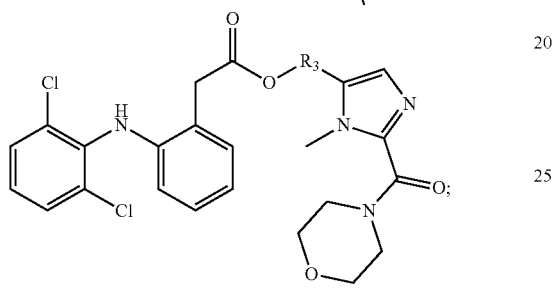
or salts, solvates or hydrates thereof.
* * * * *